US007923560B2

(12) United States Patent
Wightman et al.

(10) Patent No.: US 7,923,560 B2
(45) Date of Patent: Apr. 12, 2011

(54) DELIVERY OF IMMUNE RESPONSE MODIFIER COMPOUNDS

(75) Inventors: Paul D. Wightman, Woodbury, MN (US); Isidro Angelo E. Zarraga, Minneapolis, MN (US); Naiyong Jing, Woodbury, MN (US); Jie J. Liu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 578 days.

(21) Appl. No.: 10/821,335

(22) Filed: Apr. 9, 2004

(65) Prior Publication Data

US 2004/0258698 A1 Dec. 23, 2004

Related U.S. Application Data

(63) Continuation-in-part of application No. 10/640,904, filed on Aug. 14, 2003, now Pat. No. 7,427,629.

(60) Provisional application No. 60/462,140, filed on Apr. 10, 2003, provisional application No. 60/545,424, filed on Feb. 18, 2004, provisional application No. 60/515,256, filed on Oct. 29, 2003, provisional application No. 60/545,542, filed on Feb. 18, 2004.

(51) Int. Cl.
*C07D 471/04* (2006.01)
*A61K 31/44* (2006.01)

(52) U.S. Cl. ............ 546/82; 546/118; 546/80; 514/293; 514/300

(58) Field of Classification Search .................... 546/82, 546/118, 80; 514/293, 300, 118
See application file for complete search history.

(56) References Cited

U.S. PATENT DOCUMENTS

| | | | |
|---|---|---|---|
| 4,689,338 A * | 8/1987 | Gerster | 514/293 |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,078,978 A * | 1/1992 | Tarbet et al. | 423/22 |
| 5,175,296 A | 12/1992 | Gerster | |
| 5,238,944 A | 8/1993 | Wick et al. | |
| 5,266,575 A | 11/1993 | Gerster et al. | |
| 5,268,376 A | 12/1993 | Gerster | |
| 5,342,940 A | 8/1994 | Ono et al. | |
| 5,346,905 A | 9/1994 | Gerster | |
| 5,352,784 A | 10/1994 | Nikolaides et al. | |
| 5,367,076 A | 11/1994 | Gerster | |
| 5,376,501 A | 12/1994 | Mariën et al. | |
| 5,389,640 A | 2/1995 | Gerster et al. | |
| 5,395,937 A | 3/1995 | Nikolaides et al. | |
| 5,446,153 A | 8/1995 | Lindstrom et al. | |
| 5,447,724 A | 9/1995 | Helmus et al. | |
| 5,482,936 A | 1/1996 | Lindstrom | |
| 5,494,916 A | 2/1996 | Lindstrom et al. | |
| 5,525,612 A | 6/1996 | Gerster | |
| 5,605,899 A | 2/1997 | Gerster et al. | |
| 5,693,811 A | 12/1997 | Lindstrom | |
| 5,741,908 A | 4/1998 | Gerster et al. | |
| 5,756,747 A | 5/1998 | Gerster | |
| 5,939,090 A | 8/1999 | Beaurline et al. | |
| 6,028,076 A | 2/2000 | Hirota et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,113,918 A | 9/2000 | Johnson et al. | |
| 6,194,388 B1 | 2/2001 | Krieg et al. | |
| 6,194,425 B1 | 2/2001 | Gerster et al. | |
| 6,200,592 B1 | 3/2001 | Tomai et al. | |
| 6,207,646 B1 | 3/2001 | Krieg et al. | |
| 6,239,116 B1 | 5/2001 | Krieg et al. | |
| 6,245,776 B1 | 6/2001 | Skwierczynski et al. | |
| 6,273,913 B1 | 8/2001 | Wright et al. | |
| 6,303,347 B1 | 10/2001 | Johnson et al. | |
| 6,323,200 B1 | 11/2001 | Gerster et al. | |
| 6,329,381 B1 | 12/2001 | Kurimoto et al. | |
| 6,331,539 B1 | 12/2001 | Crooks et al. | |
| 6,339,068 B1 | 1/2002 | Krieg et al. | |
| 6,376,501 B1 | 4/2002 | Isobe et al. | |
| 6,376,669 B1 | 4/2002 | Rice et al. | |
| 6,387,938 B1 | 5/2002 | Mizuguchi et al. | |
| 6,406,705 B1 | 6/2002 | Davis et al. | |
| 6,426,334 B1 | 7/2002 | Agrawal et al. | |
| 6,440,992 B1 | 8/2002 | Gerster et al. | |
| 6,451,810 B1 | 9/2002 | Coleman et al. | |
| 6,476,000 B1 | 11/2002 | Agrawal | |
| 6,486,168 B1 | 11/2002 | Skwierczynski et al. | |
| 6,486,214 B1 | 11/2002 | Uhrich | |
| 6,514,985 B1 | 2/2003 | Gerster et al. | |
| 6,518,265 B1 | 2/2003 | Kato et al. | |

(Continued)

FOREIGN PATENT DOCUMENTS

| | | |
|---|---|---|
| EP | 0386767 | 9/1990 |
| EP | 0 394 026 | 10/1990 |
| EP | 1 104 764 A1 | 6/2001 |
| JP | 9-208584 | 8/1997 |
| JP | 11-80156 | 3/1999 |
| JP | 11-222432 | 8/1999 |
| JP | 2000-247884 | 9/2000 |
| WO | WO 00/47719 A2 | 8/2000 |
| WO | WO 00/75304 A1 | 12/2000 |
| WO | WO 00/76505 A1 | 12/2000 |

(Continued)

OTHER PUBLICATIONS

Dorwald F. A. Side Reactions in Organic Synthesis, 2005, Wiley: VCH, Weinheim p. IX of Preface.*

(Continued)

*Primary Examiner* — Rita J Desai

(57) ABSTRACT

The present invention provides immune response modifiers (IRMs) associated with (typically, attached to, and preferably, covalently attached to) macromolecular support materials. The IRM compounds in such IRM-support complexes retain biological activity. Such attachment of an IRM to a macromolecular support material provides for the localized biological activity of the IRM.

1 Claim, 1 Drawing Sheet

U.S. PATENT DOCUMENTS

| | | | |
|---|---|---|---|
| 6,518,280 B2 | 2/2003 | Gerster et al. | |
| 6,525,028 B1 | 2/2003 | Johnson et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,582,938 B1 | 6/2003 | Su et al. | 435/91.2 |
| 6,649,172 B2 | 11/2003 | Johnson | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,347 B2 | 1/2004 | Crooks et al. | |
| 6,677,348 B2 | 1/2004 | Heppner et al. | |
| 6,677,349 B1 | 1/2004 | Griesgraber | |
| 6,683,088 B2 | 1/2004 | Crooks et al. | |
| 6,894,060 B2 * | 5/2005 | Slade | 514/293 |
| 7,030,129 B2 * | 4/2006 | Miller et al. | 514/262.1 |
| 2002/0016332 A1 | 2/2002 | Slade | |
| 2002/0022721 A1 | 2/2002 | Trulson et al. | 536/25.31 |
| 2002/0055517 A1 | 5/2002 | Smith | |
| 2002/0058674 A1 | 5/2002 | Hedenstrom et al. | |
| 2002/0110840 A1 | 8/2002 | Tomai et al. | |
| 2003/0133913 A1 | 7/2003 | Tomai et al. | |
| 2003/0139364 A1 | 7/2003 | Krieg et al. | |
| 2003/0144283 A1 | 7/2003 | Coleman et al. | |
| 2003/0199461 A1 | 10/2003 | Averett et al. | |
| 2004/0010007 A1 | 1/2004 | Dellaria et al. | |

FOREIGN PATENT DOCUMENTS

| | | |
|---|---|---|
| WO | WO 00/76518 A1 | 12/2000 |
| WO | 01/00242 | 1/2001 |
| WO | 03/034944 | 1/2001 |
| WO | WO 0123067 * | 5/2001 |
| WO | WO 01/68144 | 9/2001 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/085905 A1 | 10/2002 |
| WO | WO 02/092118 | 11/2002 |
| WO | 02/102825 | 12/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/103584 A2 | 12/2003 |
| WO | 2004/060967 | 7/2004 |
| WO | WO 2005/109313 A2 | 11/2005 |

OTHER PUBLICATIONS

Langer, 1990, New methods of Drug Delivery. pp. 1527-1533.*

Testerman, et al., "Cytokine Induction by the Immunomodulators Imiquimod and S-27609", *Journal of Leukocyte Biology*, vol. 58, pp. 365-372, Sep. 1995.

Chollet, et al, "Development of a Topically Active Imiquimod Formulation", *Pharmaceutical Development and Technology*, 4(1), pp. 35-43 (1999).

Brassard et al.; "Interferon-α as an immunotherapeutic protein"; Journal of Leukocyte Biology; vol. 71; Apr. 2002; pp. 565-581.

Izumi et al.; "1*H*-imidazo[4,5-*c*]quinoline Derivatives as Novel Potent TNF-α Suppressors: Synthesis and Structure-Activity Relationship of 1-, 2-and 4-Substituted 1*H*-imidazo[4,5-*c*]quinolines or 1*H*imidazo[4,5-*c*]Pyridines"; *Bioorganic and Medicinal Chemistry*, vol. 11. pp. 2541-2550 (2003).

Drachman, "Clinical Experience with Drug-Eluting Stents," Rev Cardiovasc Med. 2002;3 (suppl 5): S31-S37.

Heldman et al., "Paclitaxel Stent Coating Inhibits Neointimal Hyperplasia at 4 Weeks in a Porcine Model of Coronary Restenosis," Circulation. 2001; 103: 2289-2295.

Lepor et al., "Effective and Efficient Strategies for Coronary Revascularization in the Drug-Eluting Stent Era," Rev Cardiovasc Med. 2002;3 (suppl 5): S38-S50).

Rensing et al., "Coronary restenosis elimination with a sirolimus eluting stent, First European human experience with 6-month angiographic and intravascular follow-up," Eur. Heart J. 2001; 22: 2125-2130.

Rogers, "Drug-Eluting Stents: Role of Stent Design, Delivery Vehicle, and Drug Selection, "Rev Cardiovasc Med. 2002; 3 (suppl 5): S10-S15.

Schwartz et al., "Pathophysiology of Coronary Artery Restenosis," Rev Cardiovasc Med. 2002; 3 (suppl 5): S4-S9.

Sousa et al., "Sustained Suppression of Neointimal Proliferation by Sirolimus-Eluting Stents, One-Year Angiographic and Intravascular Ultrasound Follow-up," Circulation, 2001; 104: 2007-2011.

Gibson S. J. et al., "Plasmacytoid dendritic cells produce cytokines and mature in response to the TLR7 agonists, imiquimod and resiquimod" *Cellular Immunology* vol. 218, pp. 74-86 (2002).

The Merck Index, An encyclopedia of chemicals, drugs, and biologicals 13th Edition, 2001, Merck & Co., Inc., Whitehouse Station, NJ, USA.

Lu Z. R. et al: "Synthesis of a Bioadhesive lectin-HPMA copolymer-cyclosporin conjugates." Biocunjugate Chem., vol. 11, Dec. 10, 1999.

Supplementary European Search from Application No. EP 04 74 9964, dated Sep. 6, 2010.

* cited by examiner

DELIVERY OF IMMUNE RESPONSE MODIFIER COMPOUNDS

CROSS-REFERENCE TO RELATED APPLICATIONS

The present application is a Continuation-In-Part of U.S. patent application Ser. No. 10/640,904, filed on Aug. 14, 2003, now U.S. Pat. No. 7,427,629 and claims priority to U.S. Provisional Patent Application Ser. No. 60/462,140, filed on Apr. 10, 2003, No. 60/545,424, filed on Feb. 18, 2004, No. 60/515,256, filed on Oct. 29, 2003, and No. 60/545,542, filed on Feb. 18, 2004, each of which is incorporated herein by reference in their entirety.

BACKGROUND

There has been a major effort in recent years, with significant successes, to discover new drug compounds that act by stimulating certain key aspects of the immune system, as well as by suppressing certain other aspects (see, e.g., U.S. Pat. Nos. 6,039,969 and 6,200,592). These compounds, referred to as immune response modifiers (IRMs), appear to act through basic immune system mechanisms known as toll-like receptors to induce selected cytokine biosynthesis and may be used to treat a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis), and $T_H2$-mediated diseases (e.g., asthma, allergic rhinitis, atopic dermatitis), and are also useful as vaccine adjuvants. Many of the IRM compounds are small organic molecule imidazoquinoline amine derivatives (see, e.g., U.S. Pat. No. 4,689,338), but a number of other compound classes are known as well (see, e.g., U.S. Pat. No. 5,446,153) and more are still being discovered. Other IRMs have higher molecular weights, such as oligonucleotides, including CpGs (see, e.g., U.S. Pat. No. 6,194,388). In view of the great therapeutic potential for IRMs, and despite the important work that has already been done, there is a substantial ongoing need for new means of controlling the delivery and activity of IRMs in order to expand their uses and therapeutic benefits.

SUMMARY

It has now surprisingly been found that immune response modifiers (IRMs) of the invention can be attached to macromolecular support materials and, importantly, that they retain biological activity even while they remain attached to such material. This ability to form biologically active IRM-support complexes allows for a tremendous range of useful applications where one may not wish to release all of the IRM compound to be effective.

For example, in contrast to eluting drug from a coated surface or delivering drug from a formulation, the IRMs here can be active while attached to, e.g., implantable medical devices, particles, beads, polymers, and other supports, substrates, and matrix materials. This approach can be used, e.g., to help reduce systemic absorption through dermal, mucosal and other tissues, such as through the GI tract, respiratory tract, eyes, rectum, bladder, vagina, etc., as well as to maintain extended deposition of the IRM at an intended site of action, such as implanted in a solid tumor mass. As an illustration, immune system dendritic cells can be removed from a patient and activated ex vivo in the presence of a desired antigen by being placed in contact with a material lined with attached IRMs (e.g., container walls, beads, mesh, etc.). The activated dendritic cells can then be conveniently returned to the patient for therapeutic use, leaving the IRM behind so as to avoid systemic exposure.

Moreover, not only has it been found that the IRMs are still biologically active when attached to a support complex, but surprisingly, the cytokine induction profile of the IRM can be altered in potentially desirable ways by virtue of such attachment. It has been found that attachment of some IRMs actually modifies the cytokine induction profile in favor of interferon α, which may be important for certain therapeutic uses.

The IRM may be covalently or non-covalently bound, preferably covalently bound, to the macromolecular support material. Attachment of an IRM to a macromolecular support material provides for the localized biological activity of the IRM and typically prevents, or at least reduces the occurrence of, the systemic distribution of the IRM.

Accordingly, the present invention provides an IRM-support complex having an IRM compound attached to a macromolecular support material. In some embodiments, the IRM compound may be covalently attached to the macromolecular support material. In this context, "macromolecular support material" refers to organic materials, inorganic materials, and combinations thereof that are generally biologically inactive relative to the biology being targeted by the IRM. The macromolecular support material is typically of a size and chemical nature to prevent the engulfment or penetration of the macromolecular material into cells, although this is not a necessary limitation. For certain embodiments, the macromolecular support material preferably has an average largest dimension of at least 1 nanometer (nm). In some embodiments, the macromolecular support material may be part of a gel, a foam, a sponge, a fiber, or a bead.

In another aspect of the invention, an IRM-support complex that includes an immune response modifier is attached to a polymer. In certain embodiments, the immune response modifier is covalently attached to the polymer. In certain embodiments, the polymer is a bioadhesive polymer. In certain embodiments, the present invention provides a medical article coated with the IRM-support complex that includes a polymer.

In another aspect, the present invention also provides a medical article (i.e., medical device such as an implantable device) including an IRM-support complex, wherein the IRM-support complex includes an immune response modifier attached to a macromolecular support material. In some embodiments, the medical article may be a stent, a shunt, an artificial valve, a suture, a surgical clip, a surgical staple, an indwelling catheter, a dental implant, an orthopedic implant, a surgical prosthetic, an implantable vascular access port, an artificial heart, a ventricular assist pump, a blood oxygenator, a blood filter, a hemodialysis unit, a hemoperfusion unit, a conduit tube within a heart lung machine, a tube within a dialysis apparatus, a tube within a plasmapheresis unit, an artificial pancreas, an artificial liver, an artificial lung, an intraocular lens, or a contact lens.

In another aspect, the present invention provides a medical article having disposed thereon an IRM, with the proviso that the medical article is not a periochip. Typically, the medical article is a stent.

In another aspect, the present invention also provides a stent, shunt, or valve having a surface with an immune response modifier attached thereto. In some embodiments, the immune response modifier may be covalently attached to the surface of the stent, shunt, or valve.

In another aspect, the present invention also provides a polymer including an immune response modifier attached thereto to form an IRM-macromolecular support complex. In some embodiments, the immune response modifier may be covalently attached. In some embodiments, a medical article may be coated with the polymer. In some embodiments, the polymer may be a hydrogel.

In another aspect, the present invention also provides a method of making an IRM-support complex by attaching an immune response modifier to a macromolecular support material. In some embodiments, the immune response modifier may be covalently attached to the macromolecular support material.

In another aspect, the present invention also provides a method of treating a viral infection in a subject by administering to the subject an IRM-support complex having an IRM compound attached to a macromolecular support material. In some embodiments, the IRM-support complex may be administered orally, nasally, ocularly, vaginally, transcutaneously, or rectally.

In another aspect, the present invention also provides a method of treating an atopic immune response in a subject by administering to the subject an IRM-support complex having an IRM compound attached to a macromolecular support material. In some embodiments, the IRM-substrate may be administered orally, nasally, vaginally, ocularly, transcutaneously, or rectally.

In another aspect, the present invention also provides a method of treating solid tumors in a subject by administering to the subject an IRM-support complex having an IRM compound attached to a macromolecular support material. In some embodiments, the IRM-substrate may be administered orally, nasally, vaginally, ocularly, transcutaneously, or rectally.

In another aspect, the present invention also provides a method of preventing restenosis in a subject by implanting into the subject a stent having a surface with an immune response modifier associated therewith (preferably, attached thereto, and more preferably, covalently attached thereto).

In another aspect, the present invention also provides a method of modifying the cytokine induction profile of an IRM by attaching the IRM to a macromolecular support complex. In some embodiments, the cytokine induction profile may be modified in favor of interferon α induction.

In another aspect, the present invention also provides a method of reducing systemic adsorption of an immune response modifier in a subject by administering to the subject an IRM-support complex, the IRM-support complex including the immune response modifier attached to a macromolecular support material.

In another aspect, the present invention also provides an IRM-support complex (or a formulation thereof) including a first immune response modifier that is attached to a macromolecular support and a second immune response modifier that is not attached to the macromolecular support material. The formulation (i.e., composition) can include a solvent and/or be in the form of a gel.

In another aspect, the present invention also provides a method of activating dendritic cells by permitting the cells contact an IRM compound attached to a support complex.

In another aspect, the present invention also provides a method of treating cervical dysplasia in a subject by applying to the cervix an IRM-support complex comprising an IRM compound attached to a macromolecular support material.

In another aspect, the present invention also provides a method of treating bladder cancer in a subject by applying to the bladder an IRM support complex comprising an IRM compound attached to a macromolecular support material.

The present invention also provides a method of making an IRM-support complex, wherein the method involves attaching an immune response modifier to a macromolecular support material. Attaching the immune response modifier can involve covalently attaching it to the macromolecular support material. The method can also involve modifying the IRM to include an alkoxysilane moiety. The IRM-modified alkoxysilane is then attached to a silicon-containing support material.

In some embodiments of the present invention, the IRM compound may be an agonist of at least one TLR, preferably an agonist of TLR6, TLR7, or TLR8. The IRM may also in some cases be an agonist of TLR9. In some embodiments of the present invention, the IRM compound may be a small molecule immune response modifier (e.g., molecular weight of less than about 1000 daltons).

In some embodiments of the present invention, the IRM compound may comprise a 2-aminopyridine fused to a five-membered nitrogen-containing heterocyclic ring, or a 4-aminopyrimidine fused to a five-membered nitrogen-containing heterocyclic ring.

In some embodiments of the present invention, the IRM compound may be imidazoquinoline amines including, but not limited to, substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including, but not limited to, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including, but not limited to, amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines. Various combinations of IRMs can be used if desired.

In some embodiments, the IRM compound may be a purine, imidazoquinoline amide, benzimidazole, 1H-imidazopyridine, adenine, or a derivative thereof.

The term "comprises" and variations thereof do not have a limiting meaning where these terms appear in the description and claims, As used herein, "a," "an," "the," "at least one," and "one or more" are used interchangeably. Thus, for example, an IRM-support complex comprising "an" IRM compound can be interpreted to mean that the complex includes at least one IRM compound.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used individually and in various combinations. In each instance, the recited list serves only as a representative group and should not be interpreted as an exclusive list.

BRIEF DESCRIPTION OF THE DRAWINGS

FIG. 1.

DETAILED DESCRIPTION OF ILLUSTRATIVE EMBODIMENTS OF THE INVENTION

Figure 1A:
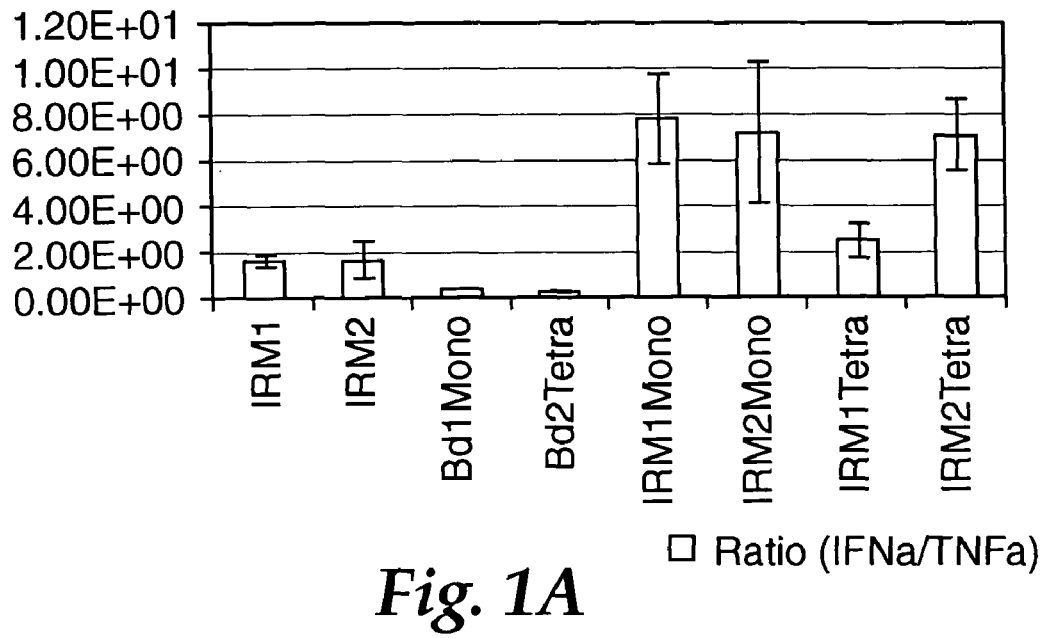
FIG. 1A is a graphical representation of the IFNα/TNFα ratio produced by human peripheral blood mononuclear cells incubated overnight with IRM1 or IRM2 bound to monomeric avidin beads or tertrameric avidin beads.

The present invention is directed to the attachment of cytokine inducing and/or suppressing immune response modifiers (IRMs) to macromolecular support materials to form IRM-support complexes. The IRMs retain biological activity following such attachment to a macromolecular support material. IRM-support complexes allow for the localized delivery of an IRM to a desired location in the body of a subject and typically prevent, or at least reduce the occurrence of, the systemic distribution of the IRM.

As used herein, "macromolecular support material" is a macromolecular material that is itself generally biologically inactive relative to the biology being targeted by the IRM. Herein, this definition of macromolecular support materials excludes bacteria and viruses, for example. The macromolecular support material may be of a size and chemical nature to prevent the engulfment or penetration of the macromolecular material into cells, in which case the IRM-support complex retains an extracellular location. Alternatively, the macromolecular support material may be of a size and chemical nature to allow engulfment by cells. For example, the macromolecular support material may be of a size and chemical nature to allow selective deposition in solid tumors on the basis of the tumor's increased vascular permeability. For certain embodiments, the macromolecular support material preferably has an average largest dimension of at least 1 nanometer (nm) (although materials having as an average largest dimension of 0.1 nm or even smaller can be used), more preferably, at least 10 nm, even more preferably, at least 100 nm, and even more preferably, at least 1 micron.

Typically, the macromolecular support material is in the form of a solid (i.e., a solid support such as particles, fibers, membranes, films), but can also be in the form of a polymeric gel, sponge, or foam, for example. A macromolecular support material can be made of a variety of materials, including substrates made of ceramic, glassy, metallic, or polymeric materials, or combinations of materials. The terms "substrate," "support material," or "support," may also be used herein to refer to a macromolecular support material.

In an IRM-support complex an IRM is attached to a macromolecular support material. As used herein, the term "attached" includes both covalent bonding and non-covalent chemical association (e.g., ionic bonding and hydrogen bonding) of an immune response modifier with a macromolecular support material. Non-covalent association is preferably by specific, high affinity protein-ligand interaction, as opposed to nonspecific hydrogen bonding. Preferably, the immune response modifiers are attached to a macromolecular support material by means of covalent bonding. The terms "coupled," "conjugated," "bonded," or "immobilized" may also be used herein to represent "attached." As used herein, "attached" excludes mere coating of the macromolecular support material with an IRM.

Attachment of an IRM to a macromolecular support material, such as solid supports (e.g., particles, fibers, and the like) as well as colloids, and polymeric foams, sponges, and gels, provides for the localized biological activity of the IRM. Also, the IRM can be attached as a side group to a polymer, and the polymer coated onto any desired surface. Although the IRM may eventually detach from the macromolecular support material (e.g., through biodegradation of a polymer to which the IRM is attached, for example), the IRM does not detach during a suitable period of use while it is active (although it may of course also be active after detachment). Such attachment of an IRM to a macromolecular support material can be used to reduce the occurrence of, or prevent, the systemic absorption of the IRM, and can minimize the systemic side effects sometimes observed with the systemic administration of an IRM. Also, such attachment of an IRM to a substrate can serve to limit or focus the effect of the IRM to a localized region for a desired duration, and if the support material can be removed, the IRM can then be easily removed at will along with it. This provides very important control over where and how long the IRM is applied.

For certain embodiments (e.g., medical articles such as stents and other implantables or extracorporeal devices), the IRM may elute from a coating on the article upon contact with a bodily fluid. In such embodiments, the IRM may be incorporated into a coating material, e.g., a polymeric material, using any of a variety of mechanisms, which may or may not include attachment of the IRM to the macromolecular support material as defined herein.

One or more IRMs can be attached to a solid support or other macromolecular support material. Also, one IRM can be attached to multiple solid supports or other macromolecular support materials.

The substrate having the IRM attached thereto can be used in a variety of medical applications, which can be therapeutic, prophylactic (e.g., as a vaccine adjuvant), or diagnostic. As used herein, "treating" a condition or a subject includes therapeutic, prophylactic, and diagnostic treatments.

For example, in certain embodiments, IRMs can be attached to the surfaces of various medical devices or implants, such as, for example, stents, shunts, artificial valves, sutures, surgical clips and staples, indwelling catheters, prosthesis, including dental and orthopedic implants and GORE-TEX surgical prosthetics, implantable vascular access ports, artificial hearts, ventricular assist pumps, extracorporeal devices such as blood oxygenators, blood filters, hemodialysis units, hemoperfusion units, conduit tubes within heart lung machines, tubes of a dialysis apparatus and plasmapheresis units, hybrid artificial organs such as pancreas or liver and artificial lungs, and the like. For example, an IRM, such as an imidazoquinolin-4-amine, can be attached to an arterial stent for use in interventional cardiology to prevent restenosis. As such, it is anticipated that the IRM would preferentially activate precursor plasmocytoid dendritic cells (pDC cells) of the blood to stimulate INFα formation, for a localized antiproliferative effect, with reduced systemic distribution of the IRM.

An IRM can be attached to a macromolecular support complex and used in wound dressings, wound packing materials, wound sealants, sutures, and surgical clips to promote healing and/or reduce the occurrence of scarring.

An IRM can be attached to a substrate used anywhere within the body, including soft tissue such as muscle or fat, hard tissue such as bone, or a cavity such as the periodontal, gastrointestinal, oral, vaginal, rectal, nasal, bladder, airway, uterus, corpus cavemosum, ocular, or a pocket such as a periodontal pocket or the cul-de-sac of the eye. Thus, the compositions of the present invention can be used to treat disorders such as respiratory disorders, gastrointestinal disorders, urological dysfunction, impotence, uterine dysfunction, and premature labor.

An IRM-support complex can be applied to the vagina or uterus to treat vaginal infections, such as, e.g., herpes or papilloma virus. For example, one or more IRMs can be attached to (as opposed to blended or dissolved in) a macromolecular support material, such as a material incorporated into a gel or foam, for application within the vagina or uterus.

An IRM-support complex can be applied to the nasal cavity. For example, one or more IRMs can be attached to a macromolecular support material, such as a gel, foam, or spray for application to the nasal passages and/or sinuses.

An IRM-support complex can be applied to the eye to treat, e.g., viral infections, such as herpes. For example, one or more IRMs can be attached to a macromolecular support material for inclusion in an ophthalmic preparation for application to the eye and/or to ophthalmic devices, such as intraocular lenses and contact lenses.

An IRM-support complex can be delivered to the gastrointestinal tract to treat gastrointestinal disorders. For example, one or more IRMs can be attached to a macromolecular support material, such as a bead, gel or foam, for delivery to the gastrointestinal tract, delivered orally or rectally.

An IRM can also be attached to a macromolecular support material, such as a polymer, for the formation of a compound depot in the body of a subject to promote the long term, localized effect of the IRM.

In some embodiments, an IRM can be attached to a macromolecular support material, such as an oligomer, a polymer, a bead, a tissue culture flask, a tissue culture plate, a microtiter plate, or a column, for use in, e.g., ex-vivo treatment of immune cells, experiment testing, or a diagnostic assay in which an IRM is a component. For example, use of an IRM-support complex can enhance cellular contact with an IRM, can facilitate the removal of an IRM from a diagnostic assay, can allow for the concentrated delivery of an IRM, and can assist in the conservation of IRM reagents. An IRM support complex can line the interior surface of an in vivo or ex vivo passage or container through which blood or other cell-containing fluid travels in order to activate immune cells without requiring systemic delivery. For example, dendritic cells can be removed from the body and matured in the presence of antigen and IRM-support complex before being delivered to the body for therapeutic use.

The methods, materials, and articles of the present invention may be applicable for any suitable subject. Suitable subjects include, but are not limited to, animals such as, but not limited to, humans, non-human primates, rodents, dogs, cats, horses, pigs, sheep, goats, cows, or birds.

In some applications, e.g., with an associated antigen, an IRM can be attached to a solid support material (e.g., a particle) or other macromolecular support material accompanied by a specific immunizing antigen on the same solid support material (e.g., particle). Alternatively, an IRM can be attached to a first solid support material (e.g., particle) or other macromolecular support material while the immunizing antigen is attached to a second solid support material (e.g., particle) or other macromolecular support material. These embodiments allow for the copresentation of an antigen and an IRM.

Suitable Immune Response Modifiers:

Immune response modifiers ("IRMs") of the present invention include compounds act on the immune system by inducing and/or suppressing cytokine biosynthesis. IRMs possess potent immunostimulating activity including, but not limited to, antiviral and antitumor activity, and can also down-regulate other aspects of the immune response, for example shifting the immune response away from a $T_H2$ immune response, which is useful for treating a wide range of $T_H2$ mediated diseases. IRMs can also be used to modulate humoral immunity by stimulating antibody production by B cells. Further, various IRMs have been shown to be useful as vaccine adjuvants (see, e.g., U.S. Pat. Nos. 6,083,505 and 6,406,705, and International Publication No. WO 02/24225).

In particular, certain IRMs effect their immunostimulatory activity by inducing the production and secretion of cytokines such as, e.g., Type I interferons, TNF-α, IL-1, IL-6, IL-8, IL-10, IL-12, MIP-1, and/or MCP-1, and can also inhibit production and secretion of certain $T_H2$ cytokines, such as IL-4 and IL-5. Some IRMs are said to suppress IL-1 and TNF (see, e.g., International Publication No. WO 00/09506).

For some embodiments, preferred IRMs are so-called small molecule IRMs, which are relatively small organic compounds (e.g., molecular weight under about 1000 daltons, preferably under about 500 daltons, as opposed to large biologic protein, peptides, and the like).

Although not bound by any single theory of activity, some IRMs are known to be agonists of at least one Toll-like receptor (TLR). IRMs that are agonists for TLRs selected from 6, 7, 8, and 9 may be particularly useful for certain applications. Some small molecule IRMs are agonists of TLRs such as 6, 7, and 8, while oligonucleotide IRM compounds are agonists of TLR9, and perhaps others. Thus, in some embodiments, the IRM that is attached to a macromolecular support material may be a compound identified as an agonist of one or more TLRs.

For example, without being bound to any particular theory or mechanism of action, IRM compounds that activate a strong cytotoxic lymphocyte (CTL) response may be particularly desirable as vaccine adjuvants, especially for therapeutic viral and/or cancer vaccines because a therapeutic effect in these settings is dependent on the activation of cellular immunity. For example, studies have shown that activation of T cell immunity in a given patient has a significant positive effect on the prognosis of the patient. Therefore the ability to enhance T cell immunity is believed to be critical to producing a therapeutic effect in these disease settings.

IRM compounds that are TLR 8 agonists may be particularly desirable for use with therapeutic cancer vaccines because antigen presenting cells that express TLR8 have been shown to produce IL-12 upon stimulation through TLR8. IL-12 is believed to play a significant role in activation of CTLs, which are important for mediating therapeutic efficacy as described above.

IRM compounds that are TLR 7 agonists and/or TLR 9 agonists may be particularly desirable for use with prophylactic vaccines because the type I interferon induced by stimulation through these TLRs is believed to contribute to the formation of neutralizing $T_H1$-like humoral and cellular responses.

IRM compounds that are both TLR 7 and TLR 8 agonists may be particularly desirable for use with therapeutic viral vaccines and/or cancer vaccines because TLR7 stimulation is believed to induce the production of type I IFN and activation of innate cells such as macrophages and NK cells, and TLR8 stimulation is believed to activate antigen presenting cells to initiate cellular adaptive immunity as described above. These cell types are able to mediate viral clearance and/or therapeutic growth inhibitory effects against neoplasms.

IRM compounds that are non-TLR 7 agonists, and do not induce substantial amounts of interferon alpha, may be desirable for use with certain vaccines such as bacterial vaccines because TLR7 induces type I IFN production, which downregulates the production of IL-12 from macrophages and DCs. IL-12 contributes to the subsequent activation of macrophages, NK cells and CTLs, all of which contribute to anti-bacterial immunity. Therefore the induction of anti-bacterial immunity against some kinds of bacteria may be enhanced in the absence of IFNα.

For purposes of the present application, one way to determine if an IRM compound is considered to be an agonist for a particular TLR is if it activates an NFκB/luciferase reporter construct through that TLR from the target species more than about 1.5 fold, and usually at least about 2 fold, in TLR transfected host cells such as, e.g., HEK293 or Namalwa cells relative to control transfectants. For information regarding TLR activation, see, e.g., International Publication Nos. WO 03/043573 and WO 03/043588, and U.S. Patent Publication Nos. US2004/0162309, US2004/0132079, US2004/0197865, US2004/0171086, and US2004/0014779, and the other IRM patents and applications disclosed herein.

Preferred IRM compounds include a 2-aminopyridine fused to a five-membered nitrogen-containing heterocyclic ring.

Certain IRMs are small organic molecules (e.g., molecular weight under about 1000 Daltons, preferably under about 500 Daltons, as opposed to large biologic protein, peptides, and the like) such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; European Patent 0 394 026; U.S. Patent Publication Nos. 2002/0016332; 2002/0055517; 2002/0110840; 2003/0133913; 2003/0199538; and 2004/0014779; and International Patent Publication Nos. WO 02/102377 and WO 03/103584.

Examples of classes of small molecule IRM compounds include, but are not limited to, compounds having a 2-aminopyridine fused to a five-membered nitrogen-containing heterocyclic ring. Such compounds include, for example, imidazoquinoline amines including, but not limited to, substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including, but not limited to, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including, but not limited to, amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

Preferred IRM compounds comprise a 2-aminopyridine fused to a five-membered nitrogen-containing heterocyclic ring.

Additional examples of small molecule IRMs said to induce interferon (among other things), include purine derivatives (such as those described in U.S. Pat. Nos. 6,376,501, and 6,028,076), imidazoquinoline amide derivatives (such as those described in U.S. Pat. No. 6,069,149), 1H-imidazopyridine derivatives (such as those described in Japanese Patent Application No. 9-255926), benzimidazole derivatives (such as those described in U.S. Pat. No. 6,387,938), derivatives of a 4-aminopyrimidine fused to a five membered nitrogen containing heterocyclic ring (such as adenine derivatives described in U.S. Pat. Nos. 6,376,501; 6,028,076 and 6,329,381; and in International Publication No. WO 02/08595), and certain 3-β-D-ribofuranosylthiazolo[4,5-d]pyrimidine derivatives (such as those described in U.S. Patent Publication No. 2003/0199461). 1H-imidazopyridine derivatives (such as those described in U.S. Pat. No. 6,518,265 and European Patent Application EP No. 1 256 582)) are said to inhibit TNF and IL-1 cytokines.

Examples of small molecule IRMs that comprise a 4-aminopyrimidine fused to a five-membered nitrogen-containing heterocyclic ring include adenine derivatives (such as those described in U.S. Pat. Nos. 6,376,501; 6,028,076 and 6,329,381; and in International Publication No. WO 02/08595).

Examples of particular IRM compounds include 2-propyl[1,3]thiazolo[4,5-c]quinolin-4-amine, which is considered predominantly a TLR 8 agonist (and not a substantial TLR 7 agonist), 4-amino-α,α-dimethyl-1H-imidazo[4,5-c]quinoline-1-ethanol, which is considered predominantly a TLR 7 agonist (and not a substantial TLR 8 agonist), and 4-amino-2-(ethoxymethyl)-α,α-dimethyl-6,7,8,9-tetrahydro-1H-imidazo[4,5-c]quinoline-1-ethanol, which is a TLR 7 and TLR 8 agonist. In addition to its TLR 7 activity (and TLR 6 activity, but low TLR 8 activity), 4-amino-α,α-dimethyl-1H-imidazo[4,5-c]quinoline-1-ethanol has beneficial characteristics, including that it has a much lower CNS effect when delivered systemically compared to imiquimod. Other examples of specific IRM compounds include, e.g., N-[4-(4-amino-2-butyl-1H-imidazo[4,5-c][1,5]naphthyridin-1-yl)butyl]-N'-cyclohexylurea, 2-methyl-1-(2-methylpropyl)-1H-imidazo[4,5-c][1,5]naphthyridin-4-amine, 1-(2-methylpropyl)-1H-imidazo[4,5-c][1,5]naphthyridin-4-amine, N-{2-[4-amino-2-(ethoxymethyl)-1H-imidazo[4,5-c]quinolin-1-yl]-1,1-dimethylethyl}methanesulfonamide, N-[4-(4-amino-2-ethyl-1H-imidazo[4,5-c]quinolin-1-yl)butyl]methanesulfonamide, 2-methyl-1-[5-(methylsulfonyl)pentyl]-1H-imidazo[4,5-c]quinolin-4-amine, N-[4-(4-amino-2-propyl-1H-imidazo[4,5-c]quinolin-1-yl)butyl]methanesulfonamide, 2-butyl-1-[3-(methylsulfonyl)propyl]-1H-imidazo[4,5-c]quinoline-4-amine, 2-butyl-1-{2-[(1-methylethyl)sulfonyl]ethyl}-1H-imidazo[4,5-c]quinolin-4-amine, N-{2-[4-amino-2-(ethoxymethyl)-1H-imidazo[4,5-c]quinolin-1-yl]-1,1-dimethylethyl}-N'-cyclohexylurea, N-{2-[4-amino-2-(ethoxymethyl)-1H-imidazo[4,5-c]quinolin-1-yl]-1,1-dimethylethyl}cyclohexanecarboxamide, N-{2-[4-amino-2-(ethoxymethyl)-1H-imidazo[4,5-c]quinolin-1-yl]ethyl}-N'-isopropylurea. Resiquimod, 4-amino-2-ethoxymethyl-α,α-dimethyl-1H-imidazo[4,5-c]quinoline-1-ethanol, may also be used in certain situations where a combination TLR 7 and TLR 8 agonist is desired.

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG and are described, for example, in International Patent Publication No. WO 00/75304.

Various combinations of IRMs can be used if desired.

Exemplary Applications:

IRMs such as imiquimod—a small molecule, imidazoquinoline IRM, marketed as ALDARA (3M Pharmaceuticals, St. Paul, Minn.)—have been shown to be useful for the therapeutic treatment of warts, as well as certain cancerous or pre-cancerous lesions (See, e.g., Geisse et al., *J. Am. Acad. Dermatol.*, 47(3): 390-398 (2002); Shumack et al., *Arch. Dermatol.*, 138: 1163-1171 (2002); U.S. Pat. No. 5,238,944 and U.S. Pat. Publication No. US2003/0199538.

Conditions that may be treated by administering an IRM-support complex of the present invention include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a *lentivirus* such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection; and (d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing would healing, including chronic wounds).

Additionally, an IRM-support complex of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Certain IRM-support complexes of the present invention may be particularly helpful in individuals having compromised immune function. For example, certain complexes may be used for treating the opportunistic infections and tumors that occur after suppression of cell mediated immunity in, for example, transplant patients, cancer patients and HIV patients.

Substrates:

Selection of a macromolecular support material to serve as a substrate for attachment of an IRM can vary widely within the scope of the invention. A macromolecular support material can be porous or nonporous, depending on preferred final use. A macromolecular support material can be continuous or non-continuous depending on ultimate desired usage. A macromolecular support material can be made of a variety of materials, which may be organic, inorganic, or combinations thereof, including substrates made of ceramic, glassy, metallic, oligomeric or polymeric materials, or combinations of materials. For certain embodiments, silicon-based materials (e.g., silica-based materials can be used). Thus, herein, the term "metal" includes metalloids such as silicon. A macromolecular support material can be flexible or inflexible depending on ultimate desired usage.

Exemplary materials include polymeric materials, such as woven and nonwoven webs (such as fibrous webs), microporous fibers, and microporous membranes.

Also, in certain embodiments, IRMs can be attached to the surface of various materials, including, but not limited to, particles (e.g., beads), films, membranes, fibers, gels, creams, foams, or sponges. Typically, such particles, films, membranes, fibers, gels, creams, foams, and sponges are organic polymeric materials.

Suitable polymers may be natural or synthetic polymers. Synthetic polymers are preferred. Herein, a polymer includes homopolymers and copolymers. A copolymer is used to refer to a polymer prepared from two or more monomers, and includes terpolymers, tetrapolymers, etc.

Exemplary synthetic polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyamides, polyvinylpyrrolidone, and polymers of lactic acid and glycolic acid, polyanhydrides, poly(ortho)esters, poly(butic acid), poly(valeric acid), and poly(lactide-cocaprolactone). Fluoropolymeric materials can also be used. Examples of such materials are disclosed in U.S. Pat. Nos. 6,630,047; 6,451,925; and 6,096,428.

Exemplary natural polymers include, but are not limited to: alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), zein, and other prolamines and hydrophobic proteins, copolymers and mixtures thereof. Copolymers and mixtures of any of these polymers could be used if desired.

The support material can be a bioadhesive polymer such as a hydrogel, including, for example, those described by H. S. Sawhney, C. P. Pathak and J. A. Hubell in Macromolecules, (1993) 26:581-587, as well as polyhyaluronic acids, casein, polysaccharides, keratin, collagen, gelatin, glutin, polyethylene glycol, crosslinked albumin, fibrin, polyanhydrides, polyacrylic acids, alginate, chitosan, poly(methyl methacrylates), poly(ethyl methacrylates), poly(butyl methacrylate), poly(isobutyl methacrylate), poly(hexyl methacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), and cellulose gums. Alternatively, polymeric hydrogel materials can be constructed from poly(vinyl alcohol) precursors as disclosed in U.S. Pat. Nos. 4,528,325 and 4,618,649 or from poly(methyl methacrylate). Poly(methyl methacrylate) is commercially available and is often used in ophthalmic devices such as intraocular lenses, contact lenses, and the like.

A suitable hydrogel can be natural, synthetic, or a combination thereof. In some embodiments, the hydrogel can be thermally responsive to a designed temperature such as, for example, a hydrogel as described in U.S. Patent Publication No. US2004/0151691. For example, the thermally responsive hydrogels can be harden when they are warmed up to body temperature, can be further harden upon UV irradiation.

Preferred bioadhesive polymers include crosslinked polymers of acrylic acid. Suitable examples include acrylic acid polymers crosslinked with allyl sucrose or allyl pentaerythriol such as those polymers designated as carbomers. Suitable carbomers include, for example, those available as CARBOPOL 971P NF Polymer and CARBOPOL 974P NF Polymer, available from Noveon, Inc., Cleveland, Ohio. Other examples of crosslinked acrylic acid polymers include those crosslinked with divinyl glycol such as those designated as polycarbophils. Suitable polycarbophils include, for example, those available as NOVEON AA-1 USP Polycarbophil, available from Noveon, Inc., Cleveland, Ohio.

Bioadhesive organic polymers are preferred for certain applications of IRMs. For example, if the IRM is to be used for treating cervical dysplasia or bladder cancer, a bioadhesive polymer is desired. Advantageously, the adhesive qualities of the formulation would allow the IRM to be in contact with the biological tissue allowing for greater contact time for cytokine induction.

Again, however, for many embodiments described herein it is important to note that the IRM is not simply dissolved or blended into a formulation from which it is to be released, but is attached to the support material by a sufficiently strong bond (which sometimes may require a covalent bond) so that under the circumstances of intended use the IRM is biologically active during use while it is attached to the support. Preferably, for certain embodiments (e.g., for bioadhesive polymeric support materials), the IRM is covalently attached to the support material. It should also be understood, however, that for each of the uses (e.g., medical articles such as stents or other implantable devices or extracorporeal devices) described herein an IRM may be provided in an unattached, releasable form, or become unattached over time, so that the IRM can be released and function in that manner. That is, for example, the IRM can be simply dissolved or blended into a macromolecular support material (e.g., as in a polymeric coating). Mixtures of the two types can also be used where desirable.

Gels, creams, films, salves, coatings, sticks, colloids, pastes, and foams incorporating IRM-support complexes can be applied to a variety of bodily surfaces, and among the many uses may include, e.g., wound dressings and wound packing materials. These sorts of solid, semi-solid, or viscous preparations can serve to promote the retention of the IRM compounds on the bodily surface and also to prevent the systemic adsorption of the IRM. Bodily surfaces can include, but are not limited to, gastrointestinal tract, vagina, uterus, bladder, oral cavity, nasal passages, periodontal surfaces, rectum, ocular surfaces, or surfaces of the ear.

Particles can be the substrate to which an IRM is attached. For example, particles can be in the form of beads, including, but not limited to carbohydrate beads and latex beads, such as those commercially available from many suppliers, including, for example Biorad and Pierce. Various oxide-containing particles (e.g., silica particles) can be used as the substrate as well. The particles can also be in the form of microparticles, such as microspheres, microcapsules, etc. Nanoparticles, such as quantum dots can be used as well.

Ceramic supports, glass supports, and metallic supports are all known in the art and are commercially available or can be prepared by a variety of known techniques.

Woven and nonwoven webs are useful as substrates having either regular or irregular physical configurations of surfaces from which the IRMs can extend. Fibrous webs are particularly desired because such webs provide large surface areas, with nonwoven fibrous webs being preferred due to ease of manufacture, low material cost, and allowance for variation in fiber texture and fiber density. A wide variety of fiber diameters, e.g., 0.05 micrometer ($\mu$m) to 50 micrometers, can be used. Web thickness can be varied widely to fit the application, e.g., 0.2 micrometer to 10 centimeters (cm) thick or more.

Fibrous webs can be prepared by methods known in the art, or by modifications of methods known in the art. Nonwoven webs can be prepared by melt-blowing as is known to those skilled in the art. In general, a molten polymeric material is extruded in such a way as to produce a stream of melt blown polymer microfibers. The fibers are collected on a collection screen, with the microfibers forming a web. The nonwoven webs can also optionally include a permeable support fabric laminated to one or both sides of the web, or can additionally contain reinforcing fibers.

Exemplary materials useful to prepare nonwoven fibrous webs include polymers and copolymers of monomers that form fibrous webs. Suitable polymers include polyalkylenes such as polyethylene and polypropylene, polyvinyl chloride, polyamides such as the various nylons, polystyrenes, polyarylsulfones, poly(vinyl alcohol), polybutylene, poly(ethylene vinyl acetate), polyacrylates such as polymethyl methacrylate, polycarbonate, cellulosics such as cellulose acetate butyrate, polyesters such as poly(ethylene terephthalate), polyimides, and polyurethanes such as polyether polyurethanes, and combinations thereof.

Nonwoven webs can also be prepared from combinations of co-extruded polymers such as polyesters and polyalkylenes. Copolymers of the monomers that provide the above-described polymers are also included within the scope of the present invention. Nonwoven webs can also be combined webs, which are an intimate blend of fine fibers and crimped staple fibers.

Suitable substrates for attachment of IRMs can also include microporous membranes, fibers, hollow fibers, or tubes, all of which are known in the art. The same materials useful for preparing webs are also suitable for preparing fibers and membranes.

An exemplary microporous membrane is one made from thermoplastic polymeric material using a thermally induced phase separation technique that involves melt blending a thermoplastic polymer with immiscible liquid at a temperature sufficient to form a homogeneous mixture, forming an article from the solution into a desired shape, cooling the shaped article so as to induce phase separation of the liquid and the polymer and to ultimately solidify the polymer, and removing at least a substantial portion of the liquid leaving a microporous polymer matrix. This method and the preferred compositions used in the method are described in detail in U.S. Pat. Nos. 4,957,943; 4,539,256; and 4,726,989. Alternatively, polymeric supports can also be hydrophobic polyolefin membranes prepared by thermally induced phase separation techniques, but also having a hydrophilic polymeric shell interlocked about such hydrophobic membrane surfaces.

The support materials having and an IRM associated therewith can include a combination of materials. For example, they can include a combination of inorganic and organic materials or a combination of different organic polymers. This can occur by layering the materials, for example. One or more of the materials can be associated (e.g., attached) to the particulate support material on the outermost surface such that an IRM is masked or hidden from a body's immune system until it reaches its targeted site of action. For example, polymers of lactic acid and glycolic acid in the form of particles having one or more IRMs attached thereto can have a coating of a polyalkylene oxide polymer (e.g., polyethylene glycol) thereon (see, e.g., Gref et al., Colloids and Surfaces B: Biointerfaces 18, 301-313, 2000). The polyalkylene oxide can function to mask the IRM from the body's immune system until it reaches its targeted site of action.

Stents:

Blood vessel occlusions are commonly treated by mechanically enhancing blood flow in the affected vessels, such as by employing a stent. Stents act as scaffoldings, functioning to physically hold open and, if desired, to expand the wall of the passageway. Typically, stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

A stent useful in the present invention can be any stent, including a self-expanding stent, or a stent that is radially expandable by inflating a balloon or expanded by an expansion member, or a stent that is expanded by the use of radio frequency which provides heat to cause the stent to change its size. The stent can also be made of any desired material, including a metallic material, a metal alloy (e.g., nickel-titanium) or even polymeric composites. The stent can have any wire or cell design. Examples of self-expanding wire mesh stents that can be used include the coronary WALL-STENT marketed by Schneider, and the SciMED RADIUS stent marketed by Boston Scientific Corp. Examples of balloon expandable stents that can be used include the MULTI-LINK stent by Guidant Corp., the Coronary Stent S670 by Medtronic AVE, the NIR stent by Boston Scientific Corp., the CROSS FLEX stent by Cordis, the PAS stent by Progressive Angioplasty Systems Inc., the V-FLEX PLUS stent by Cook, Inc., and the PALMAZ-SCHATZ crown and spiral stents by Cordis, among others. The vessels in which the stent of the present invention can be deployed include, but are not limited to, natural body vessels such as ducts, arteries, trachea, veins, intestines, bile ducts, ureters and the esophagus.

In addition to cardiac applications, the development of cancerous blockages inside body passageways (e.g., esophagus, bile ducts, trachea, intestine, vasculature and urethra, among others) can also be treated with stents, which operate to hold open passageways that have been blocked by the cancerous growth or tumors. However, such stents do not prevent the ingrowth of the cancerous material through the interstices of the stent.

In the present invention, stents are used not only for mechanical intervention but also as vehicles for providing biological therapy. Biological therapy can be achieved by attaching an IRM to the stent. Stents that have been medicated by the attachment of an IRM provide for the local administration of a therapeutic substance at the diseased site. Local delivery of an IRM is a preferred method of treatment because the substance is concentrated at a specific site and thus smaller total levels of medication can be administered in comparison to systemic dosages that often produce adverse or even toxic side effects for the subject.

Restenosis is a form of chronic vascular injury leading to vessel wall thickening and loss of blood flow to the tissue supplied by the blood vessel. It occurs in response to vascular reconstructive procedures, including virtually any manipulation that attempts to relieve vessel obstructions, such as the insertion of a stent. Restenosis is a major factor limiting the effectiveness of invasive treatments for vascular diseases and has been a major challenge to cardiovascular research for the past 15 years. According to 1994 estimates (U.S. Heart and Stroke Foundation), over 60 million Americans have one or more forms of cardiovascular disease. These diseases claimed approximately 1 million lives in the same year (41% of all deaths in the United States) and are considered the leading cause of death and disability in the developed world.

Systemic therapies that have been investigated for the prevention of restenosis include agents directed at treatment of endothelial loss, anti-platelet agents (e.g., aspirin), vasodilators (e.g., calcium channel blockers), antithrombotics (e.g., heparin), anti-inflammatory agents (e.g., steroids), agents that prevent vascular smooth muscle cell (VSMC) proliferation (e.g., colchicine), and promoters of re-endothelialization (e.g., vascular endothelial growth factor). Local treatments that have been investigated include local drug delivery (e.g., heparin) and beta and gamma radiation. All have been disappointing in human use, primarily because they appear to act on a limited portion of the restenotic process. Systemic treatments have also encountered the additional problem of achieving adequate absorption and retention of the drug at the site of the disease to provide a lasting biological effect, without causing unfavorable systemic complications and toxicities.

The inflammatory response induced by coronary angioplasty and stent placement may play a role in the development of neointimal hyperplasia, a major cause of restenosis after coronary intervention. Inflammation triggered by vascular tissue injury triggers a complex cascade of cellular and biochemical processes such as fibroblast and smooth muscle migration and proliferation, apoptosis, and matrix synthesis and remodeling. Cytokines are mediators of both the acute and chronic inflammatory response. Many cytokines such as tumor necrosis factor alpha, interferon-alpha, interferon-gamma, interleukins 1, 4, 13, and monocyte chemoattractant protein-1, and nitric oxide have been identified to play a role in the inflammatory response after vascular tissue injury. While the exact role that these and other cytokines play is not clear, there is evidence to suggest alterations in the fibroproliferative responses seen in oral, dermal and vascular tissues can be accomplished by altering the local cytokine profile in the tissue. For example interferon-alpha and gamma have been shown to reduce collagen synthesis by dermal fibroblasts and hypertrophic scar fibroblasts. In mice, interferon-gamma reduced the fibrotic response to an implanted foreign body. Interferon-gamma has also been shown to inhibit proliferation of vascular smooth muscle cells in culture and reduce arterial restenosis after balloon angioplasty.

Immune response modifiers (IRMs) include small molecules that trigger the production of cytokines from antigen presenting cells through, for example, toll-like receptor (TLR) pathways such as, for example, TLR 7 and/or 8. Some IRMs can direct the innate immune response to produce cytokines, such as IL-12 and interferon-gamma, that stimulate a $T_H1$ or cell-mediated response. This $T_H1$ cytokine response can also lead to the reduction in cytokines implicated in the $T_H2$ response. The over expression of $T_H2$ cytokines have been implicated in atopic and granulomatous conditions. Therefore, manipulation of the inflammatory reaction in vascular tissue injury with an IRM could prevent restenosis following angioplasty and stent placement.

For stents, as well as other medical devices, particularly implantable and extracorporeal devices, the IRM may elute from a coating on the article upon contact with a bodily fluid. In such embodiments, the IRM may be incorporated into a coating material, e.g., a polymeric material, using any of a variety of mechanisms, which may or may not include attachment of the IRM to the macromolecular support material. For example, the IRM can be simply mixed in a polymeric coating material.

Herein, the terms "medical device" and "medical article" are used interchangeably and refer generally to any device that has surfaces that can, in the ordinary course of their use and operation, contact bodily tissue, organs or fluids such as blood. Examples of medical devices include, without limitation, stents, stent grafts, anastomotic connectors, leads, needles, guide wires, catheters, sensors, surgical instruments, angioplasty balloons, wound drains, shunts, tubing, urethral inserts, pellets, implants, pumps, vascular grafts, valves, pacemakers, and the like. A medical device can be an extracorporeal device, such as a device used during surgery, which includes, for example, a blood oxygenator, blood pump, blood sensor, or tubing used to carry blood, and the like, which contact blood which is then returned to the subject. A medical device can likewise be an implantable device such as a vascular graft, stent, stent graft, anastomotic connector, electrical stimulation lead, heart valve, orthopedic device, catheter, shunt, sensor, replacement device for nucleus pulposus, cochlear or middle ear implant, intraocular lens, and the like. Implantable devices include transcutaneous devices such as drug injection ports and the like.

Such medical devices or medical articles do not include within their scope transdermal patches or articles used in female hygiene, such as tampons.

For certain embodiments, the medical devices include a shunt, an artificial valve, a suture, a surgical clip, a surgical staple, an indwelling catheter, a dental implant (with the proviso that the dental implant is not a periochip inserted into the periodontal cavity), an orthopedic implant, a surgical prosthetic, an implantable vascular access port, an artificial heart, a ventricular assist pump, a blood oxygenator, a blood filter, a hemodialysis unit, a hemoperfusion unit, a conduit tube within a heart lung machine, a tube within a dialysis apparatus, a tube within a plasmapheresis unit, an artificial pancreas, an artificial liver, an artificial lung, an intraocular lens, or a contact lens.

Attachment to Substrates:

IRMs can be attached to a macromolecular support material through either covalent attachment or non-covalent attachment. Non-covalent attachment of an IRM to a macromolecular support material includes attachment by ionic interaction or hydrogen bonding, for example.

One example of a non-covalent attachment included in the present invention is the well-know biotin-avidin system. Avidin-biotin affinity-based technology has found wide applicability in numerous fields of biology and biotechnology since the pioneering work by Dr. Edward Bayer and Dr. Meier Wilchek in the 1970's. The affinity constant between avidin and biotin is remarkably high (the dissociation constant, Kd, is approximately $10^{-15}$ M, see, Green, N., *Biochem J*, 89, 599, 1963) and is not significantly lessened when biotin is coupled to a wide variety of biomolecules. Numerous chemistries have been identified for coupling biomolecules to biotin with minimal or negligible loss in the activity or other desired characteristics of the biomolecule. A review of the biotin-avidin technology can be found in Applications of Avidin-Biotin Technology to Affinity-Based Separation, Bayer, et al., J. of Chromatography, 1990, pgs. 3-11.

Streptavidin, and its functional homolog avidin, are tetrameric proteins, having four identical subunits. Streptavidin is secreted by the actinobacterium *Streptomyces avidinii*. A monomer of streptavidin or avidin contains one high-affinity binding site for the water-soluble vitamin biotin and a streptavidin or avidin tetramer binds four biotin molecules.

Biotin, also known as vitamin H or cis-hexahydro-2-oxo-1H-thieno-[3,4]-imidazole-4-pentanoic acid, is a basic vitamin which is essential for most organisms including bacteria and yeast. Biotin has a molecular weight of about 244 daltons, much lower than its binding partners avidin and streptavidin. Biotin is also an enzyme cofactor of pyruvate carboxylase, trans-carboxylase, acetyl-CoA-carboxylase and beta-methylcrotonyl-CoA carboxylase which together carboxylate a wide variety of substrates.

Both streptavidin and avidin exhibit extremely tight and highly specific binding to biotin which is one of the strongest known non-covalent interactions between proteins and ligands, with a molar dissociation constant of $10^{-15}$ molar (M) (N. M. Green, Advances in Protein Chemistry, Vol. 29, pp. 85-133, 1975), and a t½ of ligand dissociation of 89 days (N. M. Green, Advances in Protein Chemistry, Vol. 29, pp. 85-133, 1975). The avidin-biotin bond is stable in serum and in the circulation (R. D. Wei, D. H. Kou, S. L. Hoo, Experientia, Vol. 27, pp. 366-368, 1970). Once formed, the avidin-biotin complex is unaffected by most extremes of pH, organic solvents and denaturing conditions. Separation of streptavidin from biotin requires conditions, such as 8M guanidine, pH 1.5, or autoclaving at 121° C. for 10 minutes.

IRMs may be biotinylated using any known methodologies. For example, IRMs may be biotinylated chemically, using activated biotin analogues, such as N-hydroxysuccinimidobiotin (NHS-biotin), which is commercially available from Pierce Chemical Company, Rockford, Ill., and requires the presence of a free primary amino group on the IRM.

Representative methods for covalent attaching an IRM to a macromolecular support material include chemical cross linkers, such as heterobifunctional cross linking compounds (i.e., "linkers") that react to form a bond between reactive groups (such as hydroxyl, amino, amido, or sulfhydryl groups) in a the immune response modifier and other reactive groups (of a similar nature) in the support material. This bond may be, for example, a peptide bond, disulfide bond, thioester bond, amide bond, thioether bond, and the like.

Immune response modifiers may be covalently bonded to a macromolecular support material by any of the methods known in the art. For example, U.S. Pat. Nos. 4,722,906, 4,979,959, 4,973,493, and 5,263,992 relate to devices having biocompatible agents covalently bound via a photoreactive group and a chemical linking moiety to the biomaterial surface. U.S. Pat. Nos. 5,258,041 and 5,217,492 relate to the attachment of biomolecules to a surface through the use of long chain chemical spacers. U.S. Pat. Nos. 5,002,582 and 5,263,992 relate to the preparation and use of polymeric surfaces, wherein polymeric agents providing desirable properties are covalently bound via a photoreactive moiety to the surface. Others have used photochemistry to modify the surfaces of biomedical devices, e.g., to coat vascular grafts. (See, e.g., Kito, H. et al., ASAIO Journal 39:M506-M511, 1993; and Clapper, D. L., et al., Trans. Soc. Biomat. 16:42, 1993). Cholakis and Sefton synthesized a polymer having a polyvinyl alcohol (PVA) backbone and heparin bioactive groups. The polymer was coupled to polyethylene tubing via nonlatent reactive chemistry, and the resultant surface was evaluated for thromboresistance in a series of in vitro and in vivo assays. (See, Cholakis, C. H. and M. V. Sefton, J. Biomed. Mater. Res. 23:399-415, 1989; and Cholakis, C. H., et. al., J. Biomed. Mater. Res. 23:417-441, 1989). Also, Kinoshita et al. disclose the use of reactive chemistry to generate polyacrylic acid backbones on porous polyethylene, with collagen molecules being subsequently coupled to carboxyl moieties on the polyacrylic acid backbones. (See Kinoshita, Y., et al., Biomaterials 14:209-215, 1993).

IRMs could be attached to macromolecular supports in a similar fashion to the methods described in U.S. Pat. Nos. 5,200,471, 5,344,701, 5,486,358, 5,510,421, and 5,907,016. These patents disclose macromolecular supports having biologically active agents covalently bound via the reaction of a nucleophilic-functional group on the biologically active agent with an azlactone functional group on the macromolecular support. In a preferred embodiment, the IRM can be attached to a macromolecular support material using a linking group. The linking group can be any suitable organic linking group that allows the substrate to be covalently coupled to the immune response modifier moiety while preserving an effective amount of IRM activity. In some embodiments, the linking group may be selected to create sufficient space between the active core of the immune response modifier moiety and the substrate that the substrate does not interfere with a biologically effective interaction between the active core and the T cells that results in IRM activity such as cytokine production.

The linking group includes a reactive group capable of reacting with a reactive group on the substrate to form a covalent bond. Suitable reactive groups include those discussed in Hermanson, G. (1996), *Bioconjugate Techniques*, Academic Press, Chapter 2 "The Chemistry of Reactive Functional Groups", 137-166. For example, the linking group may react with a primary amine (e.g., an N-hydroxysuccinimidyl ester or an N-hydroxysulfosuccinimidyl ester); it may react with a sulfhydryl group (e.g., a maleimide or an iodoacetyl), or it may be a photoreactive group (e.g. a phenyl azide including 4-azidophenyl, 2-hydroxy-4-azidophenyl, 2-nitro-4-azidophenyl, and 2-nitro-3-azidophenyl). The linking group may also be an alkoxysilyl group (e.g., a triethyoxysilyl group) that can be covalently coupled to an IRM. The alkoxysilyl group can then be covalently coupled to a silicon-containing support material such as silica, which may be in the form of particles.

The substrate includes a chemically active group accessible for covalent coupling to the linking group. A chemically active group accessible for covalent coupling to the linking group includes groups that may be used directly for covalent coupling to the linking group or groups that may be modified to be available for covalent coupling to the linking group. For example, suitable chemically active groups include, but are not limited to, primary amines and sulfhydryl groups.

Typically, attachment may occur by reacting an immune response modifier with a crosslinker and then reacting the resulting intermediate with a substrate. Many crosslinkers suitable for preparing bioconjugates are known and many are commercially available. See for example, Hermanson, G. (1996) *Bioconjugate Techniques*, Academic Press.

Attachment also may occur, for example, according to the method shown in Reaction Scheme I in which the substrate is linked to the IRM moiety through $R_1$. In step (1) of Reaction Scheme I a compound of Formula III is reacted with a heterobifunctional crosslinker of Formula IV to provide a compound of II. $R_A$ and $R_B$ each contain a functional group that is selected to react with the other. For example, if $R_A$ contains a primary amine, then a heterobifunctional crosslinker may be selected in which $R_B$ contains an amine-reactive functional group such as an N-hydroxysulfosuccinimidyl ester. $R_A$ and $R_B$ may be selected so that they react to provide the desired linker group in the conjugate.

Methods for preparing compounds of Formula III where $R_A$ contains a functional group are known. See, for example, U.S. Pat. Nos. 4,689,338; 4,929,624; 5,268,376; 5,389,640; 5,352,784; 5,494,916; 4,988,815; 5,367,076; 5,175,296; 5,395,937; 5,741,908; 5,693,811; 6,069,149; 6,194,425; 6,331,539; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; and International Publication WO 03/103584. Many heterobifunctional crosslinkers are known and many are commercially available. See for example, Hermanson, G. (1996), *Bioconjugate Techniques*, Academic Press, Chapter 5 "Heterobifunctional Cross-Linkers", 229-285. The reaction generally can be carried out by combining a solution of the compound of Formula III in a suitable solvent such as N,N-dimethylformamide with a solution of the heterobifunctional cross-linker of Formula IV in a suitable solvent such as N,N-dimethylformamide. The reaction may be run at ambient temperature. The product of Formula II may then be isolated using conventional techniques.

In step (2) of Reaction Scheme I a compound of Formula II that contains reactive group $Z_A$ is reacted with the substrate to provide the IRM-couples substrate of Formula I. In one embodiment the reaction can be carried out by combining a solution of the compound of Formula II in a suitable solvent such as dimethyl sulfoxide with the substrate. The reaction may be run at ambient temperature or at a reduced temperature (approximately 4° C.). If $Z_A$ is a photoreactive group such as a phenyl azide then the reaction mixture will be exposed to long wave UV light for a length of time adequate to effect cross-linking (e.g., 10-20 minutes). The average number of immune response modifier moieties per substrate surface area may be controlled by adjusting the amount of compound of Formula II used in the reaction.

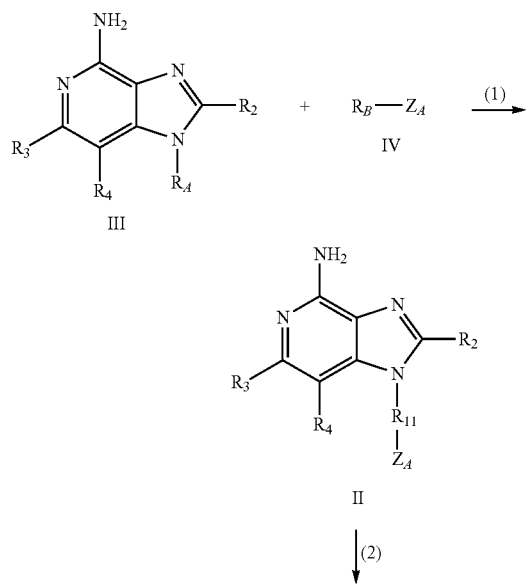

Reaction Scheme I

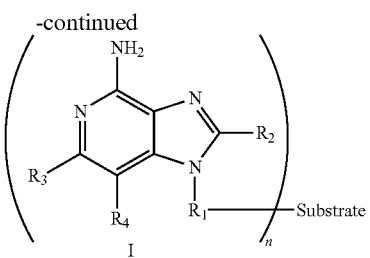

Alternatively, a compound of Formula II may be synthesized without using a heterobifunctional crosslinker. So long as the compound of Formula II contains the reactive group $Z_A$, it may be reacted with the substrate using the method of step (2) above to provide an IRM-coupled substrate.

The R groups can be hydrogen or organic groups that can optionally include various substitutions. They can include alkyl groups, alkenyl groups, including haloalkyl groups, aryl groups, heteroaryl groups, heterocyclyl groups, and the like.

For example, preferred $R_2$ groups include hydrogen, alkyl groups having 1 to 4 carbon atoms (i.e., methyl, ethyl, propyl, isopropyl, n-butyl, sec-butyl, isobutyl, tert-butyl, and cyclopropylmethyl), and alkoxyalkyl groups (e.g., methoxyethyl and ethoxymethyl). Preferably $R_3$ and $R_4$ are independently hydrogen or methyl or $R_3$ and $R_4$ join together to form a benzene ring, a pyridine ring, a 6-membered saturated ring or a 6-membered saturated ring containing a nitrogen atom. One or more of these preferred substituents, if present, can be present in the compounds of the invention in any combination.

As used herein, the terms "alkyl", "alkenyl" and the prefix "alk-" include straight chain, branched chain, and cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, and adamantyl.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring hetero atom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, isothiazolidinyl, and imidazolidinyl.

The aryl, heteroaryl, and heterocyclyl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonylthio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted", then those groups can also be substituted by one or more of the above-enumerated substituents.

In Reaction Scheme I the IRM is attached to the substrate through a linking group at the $N^1$ nitrogen of the imidazole ring. Alternatively the linking can occur at different positions on the ring system. Examples of which are shown below for imidazoquinoline amines, imidazonaphthyridine amines and imidazopyridine amines respectively.

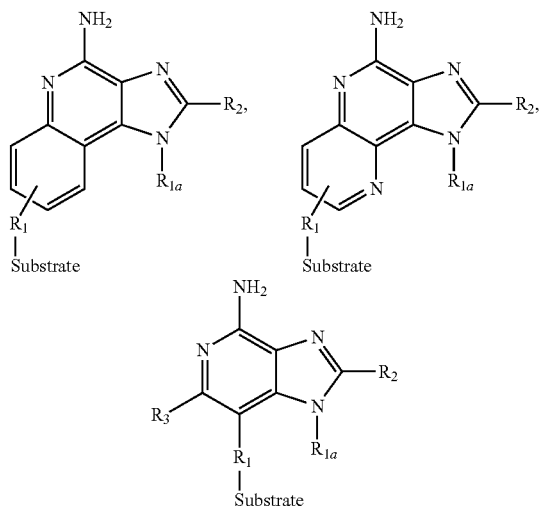

The attachment is effected using the method of Reaction Scheme I starting with an IRM containing reactive group $R_A$ at the desired attachment point.

The IRM-support complexes of the present invention can be incorporated into a wide variety of formulations, including, for example gels, creams, dispersions, or solutions. Such formulations can include solvents (e.g., propylene glycol, sorbitol, polyethylene glycol, hexylene glycol, dipropylene glycol), oils (e.g., mineral oil, vegetable oils, fatty acid triglycerides, isopropyl mysristate, isopropyl palmitate, and isostearic acid), emulsifiers (polysorbate 60, sorbitan monostearate, polyglyceryl-4oleate, polyoxyethylene(4)lauryl ether, poloxamers, and sorbitan trioleate), preservatives (e.g., methylparaben and propyl paraben), neutralizers (e.g., sodium hydroxide), etc. Examples of suitable formulations are disclosed in U.S. Pat. No. 6,245,776 and U.S. Patent Publication No. 2003/0199538. If the formulation is a gel, for example, it can be a preformed gel or formed at the application site.

An amount of an IRM-support complex effective for a given therapeutic or prophylactic application is an amount sufficient to achieve the intended therapeutic or prophylactic application. The precise amount of IRM-support complex used will vary according to factors known in the art including but not limited to the physical and chemical nature of the IRM compound, the nature of the macromolecular support material, the intended dosing regimen, the state of the subject's immune system (e.g., suppressed, compromised, stimulated), the method of administering the IRM compound, and the species to which the formulation is being administered. Accordingly it is not practical to set forth generally the amount that constitutes an amount of IRM support complex effective for all possible applications. Those of ordinary skill in the art, however, can readily determine the appropriate amount with due consideration of such factors.

The dosing regimen may depend at least in part on many factors known in the art including but not limited to the physical and chemical nature of the IRM compound, the nature of the macromolecular support material, the amount of IRM being administered, the state of the subject's immune system (e.g., suppressed, compromised, stimulated), the method of administering the IRM-support complex, and the species to which the formulation is being administered. Accordingly it is not practical to set forth generally the dosing regimen effective for all possible applications. Those of ordinary skill in the art, however, can readily determine the appropriate amount with due consideration of such factors.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

IRM Compounds

The IRM compounds used in the examples are shown in Table 1.

TABLE 1

| Compound | Chemical Name | Reference |
|---|---|---|
| IRM1 | $N^1$-[2-(4-amino-2-butyl-1H-imidazo[4,5-c]quinolin-1-yl)ethyl]-5-(2-oxoperhydrothieno[3,4-d]imidazol-4-yl)pentanamide | Example 28 U.S. Pat. No. 6,451,810 B1 |
| IRM2 | $N^1$-(6-{[4-(4-amino-2-butyl-1H-imidazo[4,5-c]quinolin-1-yl)butyl]amino}-6-oxohexyl)-6-({5-[(3aR,4R,6aS)-[2-oxoperhydrothieno[3,4-d]imidazol-4-yl)pentanoyl}amino)hexanamide | |

Preparation of IRM2

1-(4-Aminobutyl)-2-butyl-1H-imidazo[4,5-c]quinolin-4-amine (46 mg, 0.148 mmol) was dissolved with heating in anhydrous N,N-dimethylformamide (approximately 5 milliliters (mL)). The resulting solution was allowed to cool to ambient temperature. EZ-LINK Sulfo-NHS-LC-LC-Biotin (Pierce, 2×50 milligram (mg) vials, 0.149 millimole (mmol))

was added to the solution. Each vial was rinsed with anhydrous N,N-dimethylformamide (approximately 1 mL) and the rinse was added to the reaction mixture. The reaction mixture was allowed to stir at ambient temperature for about 90 minutes. The reaction mixture was concentrated under reduced pressure at 60° C. The residue was purified by flash chromatography (2×15 cm column of SiO$_2$ eluting with 10:2: 0.25 chloroform:methanol:water) to provide a colorless glass. The glass was dissolved in methanol and then concentrated to provide N$^1$-(6-{[4-(4-amino-2-butyl-1H-imidazo[4, 5-c]quinolin-1-yl)butyl]amino}-6-oxohexyl)-6-({5-[(3aR, 4R,6aS)-2-oxoperhydrothieno[3,4-d]imidazol-4-yl) pentanoyl}amino)hexanamide as a white foam.

Preparation of N-[4-(4-Amino-2-propyl-1H-imidazo [4,5-c]quinolin-1-yl)butyl]-N'-[3-(triethoxysilyl) propyl]urea

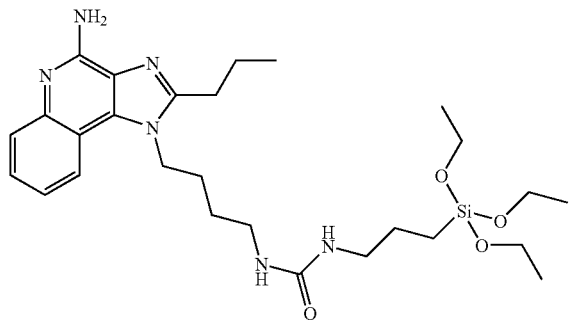

Into a flask was placed 1-(4-aminobutyl)-2-propyl-1H-imidazo[4,5-c]quinolin-4-amine (100 mg, 0.336 mmol; which can be prepared using the methods disclosed in U.S. Pat. No. 6,069,149) and 5 mL anhydrous dimethyl sulfoxide (DMSO). The mixture was stirred until the solid was completely dissolved. To the solution was slowly added 3-(triethoxysilyl)propyl isocyanate (83.2 mg, 0.336 mmol) in DMSO (1.5 mL) at room temperature. After the addition, the reaction solution was stirred overnight. The reaction solution was sampled and analyzed by NMR. The spectra showed the desired addition product, N-[4-(4-amino-2-propyl-1H-imidazo[4,5-c]quinolin-1-yl)butyl]-N'-[3-(triethoxysilyl)propyl]urea, at 100% conversion. The sample was also analyzed by liquid chromatography, the spectrum showed a single product peak with the disappearance of the starting materials.

The reaction was repeated using 15 mL of anhydrous tetrahydrofuran (THF) in place of the DMSO. Analysis of the resulting product by NMR showed 97% conversion of the starting material to the desired addition product.

Preparation of N-[3-(4-Amino-2-ethoxymethyl-6,7-dimethyl-1H-imidazo[4,5-c]pyridin-1-yl)propyl]-N'-[3-(triethoxysilyl)propyl]urea

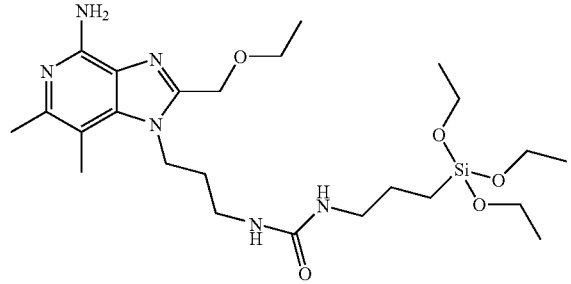

Into a flask was placed 1-(3-aminopropyl)-2-ethoxymethyl-6,7-dimethyl-1H-imidazo[4,5-c]pyridin-4-amine (100 mg, 0.36 mmol; Example 21 in U.S. Pat. No. 6,545,016) and 5 mL anhydrous dimethyl sulfoxide (DMSO). The mixture was stirred until the solid was completely dissolved. To the solution was slowly added 3-(triethoxysilyl)propyl isocyanate (89.1 mg, 0.36 mmol) in DMSO (1.5 mL) at room temperature. After the addition, the reaction solution was stirred overnight. The reaction solution was sampled and analyzed by NMR. The spectra showed the desired addition product, N-[3-(4-amino-2-ethoxymethyl-6,7-dimethyl-1H-imidazo [4,5-c]pyridin-1-yl)propyl]-N'-[3-(triethoxysilyl)propyl] urea, at 100% conversion. The sample was also analyzed by liquid chromatography, the spectrum showed a single product peak with the disappearance of the starting materials.

Preparation of 2-ethoxymethyl-1-((3-{2-hydroxy-3-[3-(trimethoxysilyl)propoxy]propyl}amino))propyl-6,7-dimethyl-1H-imidazo[4,5-c]pyridine-4-amine

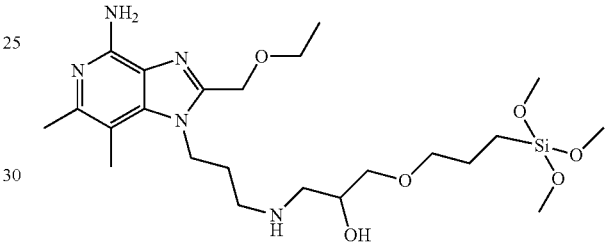

Into a flask was placed 1-(3-aminopropyl)-2-ethoxymethyl-6,7-dimethyl-1H-imidazo[4,5-c]pyridin-4-amine (10 mg, 0.036 mmol; Example 21 in U.S. Pat. No. 6,545,016) and 2.5 mL anhydrous tetrahydrofuran. The mixture was stirred until the solid was completely dissolved. To the solution was slowly added 3-glycidoxypropyltrimethoxysilane (8.51 mg, 0.036 mmol) at room temperature. After the addition, the reaction solution was stirred overnight. The reaction solution was sampled and analyzed by NMR. The spectra showed the desired addition product, 2-ethoxymethyl-1-((3-{2-hydroxy-3-[3-(trimethoxysilyl)propoxy]propyl}amino))propyl-6,7-dimethyl-1H-imidazo[4,5-c]pyridine-4-amine, at 100% conversion.

Preparation of N-{2-[4-amino-7-(6-aminohexyloxy)-2-ethoxymethyl-1H-imidazo[4,5-c]quinolin-1-yl]-1, 1-dimethylethyl}methanesulfonamide

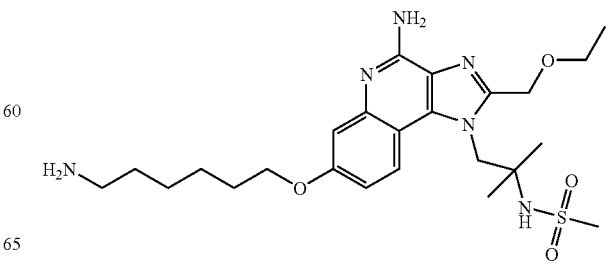

Part A

A mixture of triethyl orthoformate (92 mL, 0.55 mol) and 2,2-dimethyl-[1,3]-dioxane-4,6-dione (75.3 grams (g), 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (approximately 400 mL) until the filtrate was colorless. 5-{[(3-benzyloxy)phenylimino]methyl}-2,2-dimethyl-[1,3]-dioxane-4,6-dione (170.65 g) was isolated as a tan, powdery solid.

Part B

A mixture of 5-{[(3-benzyloxy)phenylimino]methyl}-2,2-dimethyl-[1,3]-dioxane-4,6-dione (170.65 g, 0.483 mol) and DOWTHERM A (800 mL) was heated to 100° C. and then slowly added to a flask containing DOWTHERM A (1.3 L, heated at 210° C.) over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed with diethyl ether (1.7 liters (L)) and acetone (0.5 L), and dried in an oven to provide 76.5 grams (g) of 7-benzyloxyquinolin-4-ol as a tan powder.

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 M) was slowly added over a period of 30 minutes while maintaining the reaction temperature between 121° C. and 125° C. After the addition, the reaction was stirred at 125° C. for 1 hour then allowed to cool to ambient temperature. The resulting solid was isolated by filtration, washed with water, and dried in an oven for 1.5 days to provide 69.13 g of 7-benzyloxy-3-nitroquinolin-4-ol as a grayish powder.

Part D

N,N-Dimethylformamide (100 mL) (DMF) was cooled to 0° C., and phosphorous oxychloride (27.5 mL, 0.295 mol) was added dropwise. The resulting solution was stirred for 25 minutes and then added dropwise to a mixture of 7-benzyloxy-3-nitroquinolin-4-ol (72.87 g, 0.2459 mol) in DMF (400 mL). Following the addition, the reaction was heated at 100° C. for 5 minutes, cooled to ambient temperature, and poured into ice water with stirring. A tan precipitate formed, which was isolated by filtration and dissolved in dichloromethane. The resulting solution was dried over magnesium sulfate, filtered, and concentrated under reduced pressure to yield 72.9 g of 7-benzyloxy-4-chloro-3-nitroquinoline as a light brown solid.

Part E

Triethylamine (12.8 mL, 92.0 mmol) and 1,2-diamino-2-methylpropane (5.29 mL, 50.6 mmol) were added sequentially to a solution of 7-benzyloxy-4-chloro-3-nitroquinoline (14.5 g, 46.0 mmol) in dichloromethane (400 mL). The reaction mixture was stirred overnight and then concentrated under reduced pressure. The residue was partitioned between water (200 mL) and dichloromethane (300 mL). The organic layer was washed with brine, dried over sodium sulfate, and then concentrated under reduced pressure to provide crude product as a brown solid. The crude product was passed through a layer of silica gel (eluting sequentially with chloroform and 96:4 chloroform:methanol) to provide 12.4 g of (2-amino-2-methylpropyl)(7-benzyloxy-3-nitroquinolin-4-yl)amine as a yellow solid.

Part F

Under a nitrogen atmosphere, a solution of (2-amino-2-methylpropyl)(7-benzyloxy-3-nitroquinolin-4-yl)amine (12.4 g, 33.9 mmol) in dichloromethane (400 mL) was cooled to 0° C. Triethylamine (9.43 mL, 67.8 mmol) and methanesulfonic anhydride (5.90 g, 33.9 mmol) were sequentially added, and the reaction was stirred at ambient temperature for two hours. An analysis by HPLC indicated that the reaction was incomplete, and additional methanesulfonic anhydride (1.4 g, 8.0 mmol) was added. The reaction was stirred for an additional 90 minutes, and additional methanesulfonic anhydride (0.7 g, 4 mmol) was added. The reaction was stirred for an additional three hours, and saturated aqueous sodium bicarbonate (200 mL) was added. A precipitate began to form in the organic layer, which was separated and concentrated under reduced pressure to provide a yellow solid. The solid was triturated with water (200 mL) with heating, isolated by filtration, washed with water (3×100 mL) and diethyl ether (3×50 mL), and dried overnight under vacuum to provide 14.8 g of N-[1,1-dimethyl-2-(3-nitro-7-benzyloxyquinolin-4-ylamino)ethyl]methane sulfonamide as a yellow powder.

Part G

N-[1,1-Dimethyl-2-(3-nitro-7-benzyloxyquinolin-4-ylamino)ethyl]methanesulfonamide (14.8 g, 33.3 mmol) was mixed with acetonitrile (300 mL) and added to a Parr flask; 5% platinum on carbon (2 g) was added. The reaction was flushed with nitrogen and placed under hydrogen pressure (40 pounds per square inch (psi), $2.8 \times 10^5$ Pascals (Pa)) for 5.5 hours with the hydrogen replaced after two hours. An analysis by TLC indicated the presence of starting material. Additional acetonitrile (200 mL) and 5% platinum on carbon (2 g) were added, and the reaction was placed under hydrogen pressure overnight. The reaction mixture was filtered through a layer of CELITE filter aid, and the filter cake was washed with acetonitrile. The filtrate was concentrated under reduced pressure. Toluene and dichloromethane were added and removed under reduced pressure twice to yield 12.6 g of N-[2-(3-amino-7-benzyloxyquinolin-4-ylamino)-1,1-dimethylethyl]methanesulfonamide as a solid.

Part H

Under a nitrogen atmosphere, a solution of N-[2-(3-amino-7-benzyloxyquinolin-4-ylamino)-1,1-dimethylethyl]methanesulfonamide (12.6 g, 30.4 mmol) in dichloromethane (300 mL) was cooled to approximately 0° C.; triethylamine (4.23 mL, 30.4 mmol) was added. Ethoxy acetyl chloride (3.33 mL, 30.4 mmol) was added dropwise, and the reaction was stirred at ambient temperature for 1.5 hours. The volatiles were removed under reduced pressure, and the residue was dissolved in ethanol (300 mL). Triethylamine (13 mL) was added, and the reaction was heated at reflux overnight and allowed to cool to ambient temperature. The volatiles were removed under reduced pressure. The residue was dissolved in dichloromethane (300 mL), and the resulting solution was washed with water (2×100 mL) and brine, dried over sodium sulfate, filtered, and concentrated under reduced pressure to provide a brown oil. The oil was purified by column chromatography on silica gel (eluting with 97.5:2.5 chloroform:methanol) to provide 12.4 g of N-[2-(7-benzyloxy-2-ethoxymethyl-1H-imidazo[4,5-c]quinolin-1-yl)-1,1-dimethylethyl]methanesulfonamide as a beige solid.

Part I

A solution of N-[2-(7-benzyloxy-2-ethoxymethyl-1H-imidazo[4,5-c]quinolin-1-yl)-1,1-dimethylethyl]methanesulfonamide (9.38 g, 19.5 mmol) in ethanol (150 mL) was added to a Parr vessel containing 10% palladium on carbon (0.83 g). The reaction was placed under hydrogen pressure (50 psi, $3.4 \times 10^5$ Pa) over two nights. Starting material remained as evidenced by a TLC analysis, and additional 10% palladium on carbon (1.02 g) was added. The reaction was continued for an additional eight hours. The reaction mixture was filtered through a layer of CELITE filter aid, and the filter cake was washed with ethanol and methanol. The filtrate was concentrated under reduced pressure, and the residue was several times dissolved in toluene and concentrated under reduced pressure to yield a yellow powder, which was dried under high vacuum to provide 7.37 g of N-[2-(2-ethoxymethyl-7-hydroxy-1H-imidazo[4,5-c]quinolin-1-yl)-1,1-dimethylethyl]methanesulfonamide as a yellow solid.

Part J

Under a nitrogen atmosphere, cesium carbonate (9.18 g, 28.2 mmol) was added in a single portion to a solution of N-[2-(2-ethoxymethyl-7-hydroxy-1H-imidazo[4,5-c]quinolin-1-yl)-1,1-dimethylethyl]methanesulfonamide (7.37 g, 18.8 mmol) in DMF. A solution of tert-butyl 6-iodohexylcarbamate (6.75 g, 20.6 mmol) in DMF (approximately 100 mL) was added. The reaction mixture was heated overnight at 65° C. and then concentrated under reduced pressure to provide an orange oil. The oil was partitioned between water (300 mL) and dichloromethane (300 mL). The organic layer was washed sequentially with water (×2) and brine, dried over sodium sulfate, filtered, and then concentrated under reduced pressure. The residue was dissolved in dichloromethane (100 mL), washed sequentially with water (×10) and brine, dried over sodium sulfate, filtered, and then concentrated under reduced pressure to provide 10.85 g of crude product as a yellow foam. The crude product was purified by column chromatography on silica gel (eluting sequentially with 95:5 and 92.5:7.5 dichloromethane:methanol) to provide 8.5 g of tert-butyl {6-[2-ethoxymethyl-1-(2-methanesulfonylamino-2-methylpropyl)-1H-imidazo[4,5-c]quinolin-1-yloxy]hexyl}carbamate as a white solid.

Part K

3-Chloroperoxybenzoic acid (4.23 g of 60%, 14.4 mmol) was added in a single portion to a solution of tert-butyl {6-[2-ethoxymethyl-1-(2-methanesulfonylamino-2-methylpropyl)-1H-imidazo[4,5-c]quinolin-1-yloxy]hexyl}carbamate (8.5 g, 14.4 mmol) in chloroform (200 mL). The reaction mixture was stirred for several hours and then washed sequentially with 1% sodium carbonate (×2) and brine. The organic layer was dried over sodium sulfate, filtered, and then concentrated under reduced pressure to provide 9.20 g of tert-butyl {6-[2-ethoxymethyl-1-(2-methanesulfonylamino-2-methylpropyl)-5-oxido-1H-imidazo[4,5-c]quinolin-1-yloxy]hexyl}carbamate as a orange solid.

Part L

Ammonium hydroxide (20 mL) and p-toluenesulfonyl chloride (2.74 g, 14.4 mmol) were added sequentially with rapid stirring to a mixture of the material from Part K in dichloromethane (150 mL), and the reaction was stirred for two hours. The organic layer was then washed with saturated aqueous sodium bicarbonate (2×) and brine, dried over sodium sulfate, filtered, and concentrated under reduced pressure to provide tert-butyl {6-[4-amino-2-ethoxymethyl-1-(2-methanesulfonylamino-2-methylpropyl)-1H-imidazo[4,5-c]quinolin-1-yloxy]hexyl}carbamate as a red solid.

Part M

A solution of the material from Part L in hydrochloric acid in ethanol (50 mL of 4.25 M) was heated to reflux and then allowed to cool to ambient temperature. The reaction mixture was purged with nitrogen for approximately 1 hour and then concentrated under reduced pressure. The residue was dissolved in water and then washed with chloroform (×2). The pH of the aqueous layer was adjusted with ammonium hydroxide and then the aqueous layer was extracted with chloroform (×3). The combined extracts were washed with brine, dried over sodium sulfate, filtered, and then concentrated under reduced pressure to provide 6.86 g of N-{2-[4-amino-7-(6-aminohexyloxy)-2-ethoxymethyl-1H-imidazo[4,5-c]quinolin-1-yl]-1,1-dimethylethyl}methanesulfonamide as a tan solid.

Example 1

IRM1 and IRM2, each containing a biotin moiety, were coupled to ULTRALINK immobilized monomeric avidin beads (item number 53146, PIERCE Biotechnology, 3737 N. Meridian Road, P.O. Box 117, Rockford Ill.) and ULTRALINK immobilized NEUTRAVIDIN tetrameric avidin beads (item number 53140, PIERCE Biotechnology, Rockford, Ill.) in the following manner. An aliquot (3.48 µL) of a 50 mM IRM stock solution in dimethyl sulfoxide was added to 1 mL of the bead suspension. The resulting suspension was allowed to incubate at ambient temperature for 4 hours. The beads were allowed to settle and a portion (400 µL) of the supernatant was removed. The beads were then washed using the following procedure. Phosphate buffered saline (1.4 mL) was added, the suspension was mixed by vortexing, the beads were allowed to settle, and then supernatant (1.4 mL) was removed. The wash procedure was repeated 5 times and then the beads were resuspended to 1 mL to provide a solids concentration of 50%.

Figure 1B:
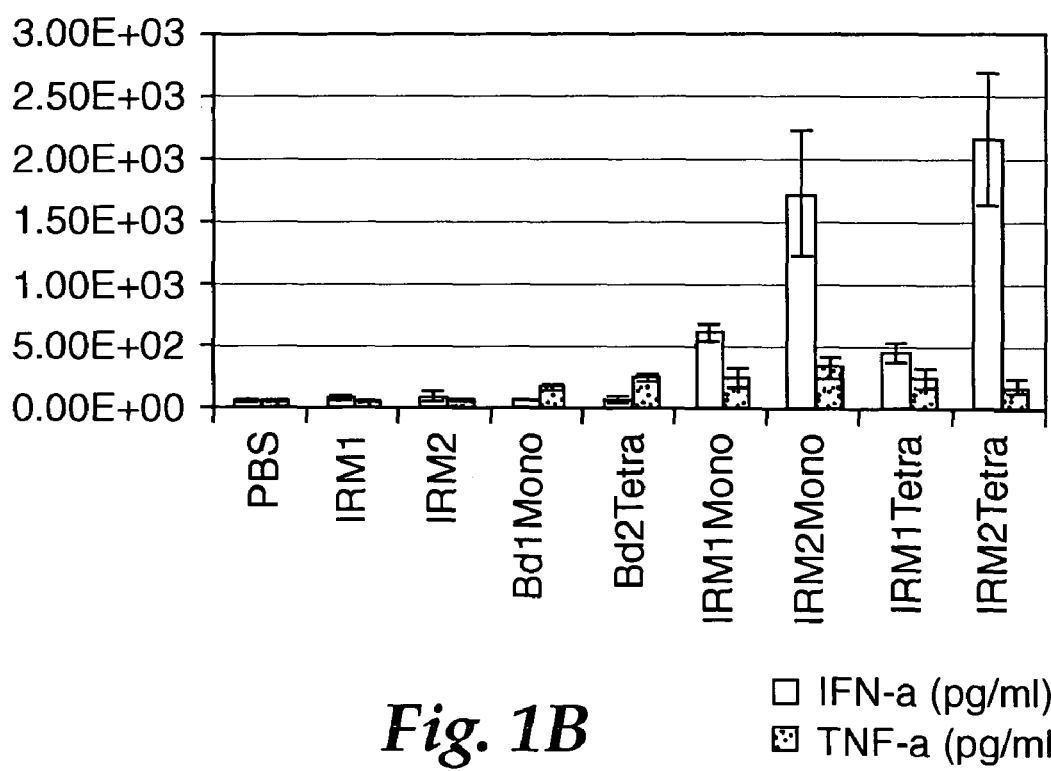
FIG. 1B is a graphical representation of the IFNα and TNFα produced by human peripheral blood mononuclear cells incubated overnight with IRM1 or IRM2 bound to monomeric avidin beads or tertrameric avidin beads.

Twenty microliters (20 µL) of each of each compound (0.7 µM IRM in 50% slurry) was added to 1 ml of human peripheral blood mononuclear cells (HPBMC) ($2 \times 10^6$ cells/ml) in RPMI complete media and incubated overnight. 1:1 dilution duplicates and 1:2 dilution duplicates were assayed for IFNα and TNFα concentrations by ELISA. Results are shown in FIG. 1. PBS represents the PBS buffer control; Bd1Mono represents the monomeric avidin bead control (50% slurry); Bd2Tetra represents the tetrameric avidin bead control (50% slurry); IRM1 represents 0.7 µM unbound IRM1; IRM2 represents 0.7 µM unbound IRM2; IRM1Mono represents IRM1 bound on Bd1 (0.7 µM IRM in 50% slurry); IRM2Mono represents IRM2 bound on Bd1 (0.7 µM IRM in 50% slurry); IRM1Tetra represents IRM1 bound on Bd2 (0.7 µM IRM in 50% slurry); and IRM2Tetra represents IRM2 bound on Bd2 (0.7 µM IRM in 50% slurry).

The values shown correspond to the average concentration from the quadruplicate experiments (dilution factor was used to adjust). Standard deviations are shown.

Example 2

Preparation of IRM Grafted Nanoparticles

A dispersion of $SiO_2$ particles (0.49 g of 2327, 20 nanometers (nm) ammonium stabilized colloidal silica sol, 41% solids; Nalco, Naperville, Ill.) was placed in a 5 mL vial. The dispersion was diluted with 0.2 g of deionized water and 0.5 g of DMSO. To the stirred dispersion was added 33 mg of N-[3-(4-amino-2-ethoxymethyl-6,7-dimethyl-1H-imidazo[4,5-c]pyridin-1-yl)propyl]-N'-[3-(triethoxysilyl)propyl]urea in 2 g of DMSO. After the addition, the dispersion was placed in an ultrasonic bath at 40° C. for 2 hours. The vial was then capped and placed in an oven at 80° C. for 24 hours. The resulting dispersion was analyzed by liquid chromatography. The spectrum showed a broad peak with different retention time compared to that of the starting IRM silane. The dispersion was centrifuged to remove the solvents.

Example 3

Preparation of IRM Grafted Nanoparticles

A dispersion of $SiO_2$ particles (0.49 g of 2327, 20 nm ammonium stabilized colloidal silica sol, 41% solids; Nalco, Naperville, Ill.) was placed in a 5 mL vial. The dispersion was diluted with 0.2 g of deionized water and 0.5 g of DMSO. To the stirred dispersion was added 33 mg of N-[3-(4-amino-2-ethoxymethyl-6,7-dimethyl-1H-imidazo[4,5-c]pyridin-1-yl)propyl]-N'-[3-(triethoxysilyl)propyl]urea in 2 g of DMSO. After the addition, the dispersion was placed in an ultrasonic bath at 40° C. for 2 hours. The vial was then capped and placed in an oven at 80° C. for 24 hours. The vial was cooled to room temperature and to the vial was added PEG triethoxysilane (12.4 mg, 0.0248 mmol available from GELEST, INC., Morrisville, Pa.). After the addition, the vial was capped and placed in an ultrasonic bath for 2 hours. The vial was then placed in an oven at 80° C. for 24 hours. The dispersion was then centrifuged to remove the solvents.

Example 4

Preparation of IRM Grafted Nanoparticles

The procedure of Example 3 was repeated except that the amount of N-[3-(4-amino-2-ethoxymethyl-6,7-dimethyl-1H-imidazo[4,5-c]pyridin-1-yl)propyl]-N'-[3-(triethoxysilyl)propyl]urea was reduced from 33 mg to 17 mg.

Example 5

Preparation of IRM Grafted Nanoparticles

The procedure of Example 3 was repeated except that the amount of N-[3-(4-amino-2-ethoxymethyl-6,7-dimethyl-1H-imidazo[4,5-c]pyridin-1-yl)propyl]-N'-[3-(triethoxysilyl)propyl]urea was reduced from 33 mg to 8.5 mg.

Example 6

Preparation of IRM Grafted Nanoparticles

The procedure of Example 3 was repeated except that the amount of PEG triethoxysilane was increased from 12.4 mg to 31.0 mg.

Example 7

Preparation of IRM Grafted Nanoparticles

The procedure of Example 2 was repeated except that 34 mg of N-[4-(4-amino-2-propyl-1H-imidazo[4,5-c]quinolin-1-yl)butyl]-N'-[3-(triethoxysilyl)propyl]urea was used in lieu of N-[3-(4-amino-2-ethoxymethyl-6,7-dimethyl-1H-imidazo[4,5-c]pyridin-1-yl)propyl]-N'-[3-(triethoxysilyl)propyl]urea.

Example 8

Preparation of IRM Grafted Nanoparticles

The procedure of Example 3 was repeated except that 34 mg of N-[4-(4-amino-2-propyl-1H-imidazo[4,5-c]quinolin-1-yl)butyl]-N'-[3-(triethoxysilyl)propyl]urea was used in lieu of N-[3-(4-amino-2-ethoxymethyl-6,7-dimethyl-1H-imidazo[4,5-c]pyridin-1-yl)propyl]-N'-[3-(triethoxysilyl)propyl]urea.

Example 9

Preparation of IRM Grafted Nanoparticles

The procedure of Example 8 was repeated except that the amount of N-[4-(4-amino-2-propyl-1H-imidazo[4,5-c]quinolin-1-yl)butyl]-N'-[3-(triethoxysilyl)propyl]urea was reduced from 34 mg to 17 mg.

Example 10

Preparation of IRM Grafted Nanoparticles

The procedure of Example 8 was repeated except that the amount of N-[4-(4-amino-2-propyl-1H-imidazo[4,5-c]quinolin-1-yl)butyl]-N'-[3-(triethoxysilyl)propyl]urea was reduced from 34 mg to 8.5 mg.

Example 11

Preparation of IRM Grafted Nanoparticles

The procedure of Example 8 was repeated except that the amount of PEG triethoxysilane was increased from 12.4 mg to 31.0 mg.

Example 12

Preparation of an IRM Grafted Fluoropolymer Film

Glass microscope slides (5.1 cm by 7.6 cm) were cleaned with acetone and distilled water. One surface of the glass substrate was coated with a THF solution containing N-[3-(4-amino-2-ethoxymethyl-6,7-dimethyl-1H-imidazo[4,5-c]pyridin-1-yl)propyl]-N'-[3-(triethoxysilyl)propyl]urea at 1 percent by weight (wt-%), and a piece of fluoropolymer Teflon FEP film, a copolymer of tetrafluoroethylene and hexafluoropropylene, available from E.I DuPont de Nemours and Company, (5.1 cm by 7.6 cm at 1 mil thickness) was subsequently laminated onto the coated substrate in a manner that assured good surface contact. The laminated sample was placed under a photoreactor consisting of 6 germicidal lamps (G15T8 bulb, 15 W, available from General Electric Company, Nela Park, Cleveland, Ohio). The laminated sample was placed 7.6-10 cm away from the bulbs with fluoropolymer film facing the UV lamps. The sample was subjected to UV irradiation for 10 min. After irradiation, the treated fluoropolymer film was removed and immersed in THF for 2 hours. The film was removed from the THF and subjected to further washing with THF. The film was dried under a stream of $N_2$ gas. The grafted film was sampled and analyzed by ESCA:

| Surface Composition: | | | | |
|---|---|---|---|---|
| Controlled sample FEP | F | C | O | N |
| | 68 | 32 | | |
| Treated sample FEP | 28 | 58 | 6 | 9 |

Example 13

Preparation of an IRM Grafted Fluoropolymer Film

Glass microscope slides (5.1 cm by 7.6 cm) were cleaned with acetone and distilled water. One surface of the glass substrate was coated with a methanol solution containing 10 wt-% of 3-aminopropyl triethoxysilane and 5 wt-% of n-phenyl propyl triethoxy silane (both are available form GELEST, INC. 11 Steel Rd. East Morrisville, Pa.), and a piece of fluoropolymer Teflon FEP film a copolymer of tetrafluoroethylene and hexafluoropropylene, available from E.I DuPont de Nemours and Company, (5.1 cm by 7.6 cm at 1 mil thickness) was subsequently laminated onto the coated substrate in a manner that assured good surface contact. The laminated sample was placed under a photoreactor consisting of 6 G15T8 bulbs. The laminated sample was placed 7.6-10 cm away from the bulbs with fluoropolymer film facing the UV lamps. The sample was subjected to UV irradiation for 3 min. After irradiation, the treated fluoropolymer film was removed and immersed in methanol for 2 hours to remove any residual primers. The film was removed from the methanol and subjected to further washing with methanol. The resulting triethoxyoxysilane grafted FEP film was then coated with a solution of N-[4-(4-amino-2-propyl-1H-imidazo[4,5-c]quinolin-1-yl)butyl]-N'-[3-(triethoxysilyl)propyl]urea in DMSO (1 wt-%) and subsequently subjected to heat treatment in an oven at 50° C. overnight. The grafted fluoropolymer film was then thoroughly washed with THF and methanol.

Example 14

Preparation of an IRM Self Assembled Monolayer

A glass microscope slide was cleaned with $H_2O_2$/concentrated sulfuric acid in a 1:3 mixture and subsequently washed with distilled water. The cleaned glass slide was immersed in a solution of N-[3-(4-amino-2-ethoxymethyl-6,7-dimethyl-1H-imidazo[4,5-c]pyridin-1-yl)propyl]-N'-[3-(triethoxysilyl)propyl]urea in DMSO (1 wt-%) for 30 min. The slide was removed and heated at 80° C. for 30 min. Finally the slide was rinsed with methanol to remove the excess N-[3-(4-amino-2-ethoxymethyl-6,7-dimethyl-1H-imidazo[4,5-c]pyridin-1-yl)propyl]-N'-[3-(triethoxysilyl)propyl]urea solution.

Example 15

IRMs were covalently coupled to gold particles to form nanometer-sized IRM-gold conjugates through a two-step reaction: the gold surface was functionalized with carbonate by reacting with thiol carbonate; the carbonate functional group was then coupled to the primary amine group of an IRM catalyzed by a carbodiimide.

Briefly, ten micro-liters of 100 mM solution of mercaptoacetic acid (catalog no. 10,900-2, Aldrich, Milwaukee, Wis.) were added to one mL of colloidal gold particles solution (approximately 10 nanomolar (nM), catalog no.: 154015, average size=40 nm, from ICN Biomedicals Inc., Aurora, Ohio). Under a nitrogen atmosphere, the mixture was shaken at 3 Hz for 3 hours (hr) at room temperature.

Twenty micro-liters of 10 mg/L PBS buffer (pH 7.2) solution of an imidazoquinoline IRM compound (4-amino-2-ethoxymethyl-1H-imidazo[4,5-c]quinoline-1-ethanamine, disclosed in U.S. Pat. No. 6,069,149), 20 microliters of freshly made 50 milligrams per liter (mg/L) PBS buffer solution of 1-ethyl-3-(3-dimethylaminopropyl carbodiimide) (EDC, HCl salt, Pierce, Rockford, Ill.), and one drop of approximately 1N HCl, were then added to the mixture. The final mixture was shaken at 3 Hz at room temperature for another 12 hours (hr) followed by centrifugation at 14,000 revolutions per minute (rpm) for 30 minutes (min). After removing the supernatant, the precipitant was washed with 0.5 mL of PBS buffer twice before being redispersed in 1 millilter (mL) of PBS. A Field Emission SEM micrograph showed that, the modified particles were well separated and distributed. The infrared spectrum showed that there was a significant increase at the —NH— signal, indicating the successful coupling of IRM to the colloidal gold.

Example 16

Similarly, a gold conjugate was also made with 10 nm colloidal gold (catalog number: 154011, ICN Biomedicals).

Example 17

IRM-gold particles was also made from avidin-biotin or anti biotin-biotin coupling: reacting the commercially available gold-strepavidin (Amersham Biosciences, Nanoprobes, Inc. Stoney Brook, N.Y.) or anti-biotin Nanogold Fab' conjugate (Nanoprobes, Inc. Stoney Brook, N.Y.) with the biotin complex of Example 29 of U.S. Pat. No. 6,451,810, which is comparable to the uncomplexed IRM in stimulating TNF release, but superior in IL-6 stimulation.

Example 18

An IRM conjugate of ferritin, a metaloprotein containing 4000 to 5000 $Fe^{3+}$ ions, was synthesized through direct coupling between the carboxyl group of [(4-amino-1-isobutyl-1H-imidazo[4,5-c]quinolin-2-yl)methoxy]acetic acid and the primary amine of ferritin catalyzed by 1-ethyl-3-(3-dimethylaminopropyl)carbodiimide (EDC).

Five milliliters of a solution of [(4-amino-1-isobutyl-1H-imidazo[4,5-c]quinolin-2-yl)methoxy]acetic acid in pH 7.4 PBS buffer (0.4 g/L) was added to a mixture of 3 ml of 50 g/L of ferritin in pH 7.4 PBS buffer solution from ICN Biochemedicals Inc., Aurora, Ohio, 2 mL of 20 mM EDC, and 10 drops of 1N HCl. After a 5-second vortex mixing, the mixture was allowed to react overnight. The mixture was then eluted through a size-exclusion liquid chromatography (PD-10) column. The brown-colored fraction was collected. The average ratio of [(4-amino-1-isobutyl-1H-imidazo[4,5-c]quinolin-2-yl)methoxy]acetic acid to ferritin in the conjugate was determined to be 0.6 (M/M), based on the UV spectrum measurement of [(4-amino-1-isobutyl-1H-imidaz[4,5-c]quinolin-2-yl)methoxy]acetic acid in the initial solution and the eluted solution. The recovery rate of ferritin was 95% after passing through the column. The eluted fraction was verified by HPLC, which showed a single peak. No significant lost of iron was observed during the modification. The conjugate showed biological activities in a test with RAW cells.

Example 19

An IRM was covalently immobilized onto functionalized superparamagnetic particles using a modified protocol based on the manufacturer's suggested protocol. Briefly, one hundred milligrams of freeze-dried DYNABEADS M-270 Epoxy (from Dynal Biotect, Lake Success, N.Y., containing approximately $6.7 \times 10^9$ beads) was suspended in 7 mL of de-ionized water. After being vortexed for 30 seconds and incubated for 10 minutes, the mixture was centrifuged at 3000 Gravity (G) for 10 minutes (min) and the supernatant was discarded.

Three milliliters of a freshly prepared solution (0.4 g/L) of 1-(4-aminobutyl)-2-butyl-1H-imidazo[4,5-c]quinolin-4-amine (which can be prepared using the methods disclosed in U.S. Pat. No. 6,069,149) in carbonate-bicarbonate buffer (0.1 M, pH 9.4) and 5 mL of 4 M ammonium sulfate in de-ionized water were added to the beads. The mixture was vortexed for 30 seconds and then placed on a shaker operating at 10 Hz at room temperature for 24 hours.

The mixture was centrifuged at 3000 G for 10 min. The supernatant was removed and the IRM concentration was determined by UV absorption at 247 nm. The beads were washed with 7 mL of methanol 3 times and 7 ml of Dulbecco's PBS 3 times. The IRM content in the modified beads was calculated by subtracting the amount of IRM found in the supernatant and washes from the amount of IRM that was initially combined with the beads.

Example 20

An IRM was covalently immobilized onto nanosized superparamagnetic particles using the following procedure.

A portion (0.1 mL) of water-based ferrofluid (EMG 304, Nashua, N.H.), a water based dispersion of iron oxide particles with dimensions in the range of 5-15 nm, was diluted with 4 mL de-ionized water and 20 mL 2-propanol. Under continuous mechanical stirring, 0.3 mL ammonia (30 wt-%, Aldrich) and 8.5 mg of N-[3-(4-amino-2-ethoxymethyl-6,7-dimethyl-1H-imidazo[4,5-c]pyridin-1-yl)propyl]-N'-[3-(triethoxysilyl)propyl]urea was slowly added to the dispersion. The reaction was allowed to proceed at room temperature for 4 hours under continuous stirring. After the reaction was complete, the IRM-attached magnetic particles were concentrated using a magnet.

Example 21

An IRM was covalently attached to core shell superparamagnetic particles using the following procedure. A portion (1 mL) of water-based silica coated superparamagnetic particles (50 mg, SiMAG-1, Chemicell Gmbh, Berlin, Germany) a water based dispersion of core shell magnetic particles with dimensions in the range of 100 nm, was diluted with 5 mL de-ionized water and 15 mL 2-propanol. Under continuous mechanical stirring, 0.3 mL ammonia (30 wt-%, Aldrich) and 8.5 mg of N-[3-(4-amino-2-ethoxymethyl-6,7-dimethyl-1H-imidazo[4,5-c]pyridin-1-yl)propyl]-N'-[3-(triethoxysilyl)propyl]urea was slowly added to the dispersion. The reaction was allowed to proceed at room temperature for 4 hours under continuous stirring. After the reaction was complete, the IRM-attached magnetic particles were concentrated using a magnet.

Example 22

An IRM can be covalently attached to a bioadhieve polymer as follows:

IRMs can be covalently attached to bioadhesive crosslinked polymers of acrylic acid through amide or ester formation. An IRM containing a pendant amine or hydroxyl group is reacted with a free carboxylic acid group on the polymer to form an amide or an ester respectively. IRM compounds containing pendant amine or hydroxyl groups and methods of making them are known. See, for example, U.S. Pat. Nos. 4,689,338; 5,389,640; 5,268,376; 6,451,810; 6,677,349; 6,660,747; 5,352,784; 5,446,153; 6,545,016; 6,194,425; 4,988,815; 5,175,296; 5,395,937; 5,741,908; and 5,693,811; U.S. Patent Publication Nos. 2004/0147543, 2004/0010007 and 2003/0232852. Bioadhesive crosslinked polymers of acrylic acid are commercially available; for example, CARBOPOL 971P and CARBOPOL 974P, both from Noveon, Inc, Cleveland, Ohio.

This IRM-bioadhesive polymer complex and other suitable complexes, designated as $(IRM)_x(Polymer)_y$, can be incorporated into a gel, cream, or solution formulation. Such formulations can include solvents, oils, emulsifiers, etc. Examples of suitable formulations are disclosed in U.S. Pat. No. 6,245,776 and U.S. Patent Publication No. 2003/0199538.

General examples of formulations of such IRM-bioadhesive polymer complexes are as follows:

| General Example of Solution and Gel Formulations | |
| --- | --- |
| Component | Ingredient Range (wt-%) |
| $(IRM)_x(Polymer)_y$ | 0.01–8.0 |
| Solvent | 0–30 |
| Preservative | 0.01–1.0 |
| Water | Qs to 100 |

| General Example of Gel Formulations | |
| --- | --- |
| Component | Ingredient Range (wt-%) |
| $(IRM)_x(Polymer)_y$ | 0.01–8.0 |
| Solvent | 0–30 |
| Preservatives | 0.01–1.0 |
| NaOH (20%) | Adjust to desired pH |
| Water | Qs to 100 |

| General Example of Cream Formulations | |
| --- | --- |
| Component | Ingredient Range (wt-%) |
| $(IRM)_x(Polymer)_y$ | 0.01–8.0 |
| Oil | 1–30 |
| Preservatives | 0.01–1.0 |
| Emulsifiers | 0.05–50 |
| Water | Qs to 100 |

Specific examples of formulations of such IRM-bioadhesive polymer complexes are as follows:

| Specific Example of Solution Formulation | | |
| --- | --- | --- |
| Component | Function | Ingredient Range (wt-%) |
| $(IRM)_x(Polymer)_y$ | Active | 2.0 |
| Propylene Glycol | Solvent | 5.0 |
| Methylparaben | Preservative | 0.15 |
| Propylparaben | Preservative | 0.03 |
| Water | Diluent | 92.82 |

Specific Example of Gel Formulation

| Component | Function | Ingredient Range (wt-%) |
|---|---|---|
| (IRM)$_x$(Polymer)$_y$ | Active | 0.5 |
| Hexylene Glycol | Solvent | 15.0 |
| Methylparaben | Preservative | 0.15 |
| Propylparaben | Preservative | 0.03 |
| NaOH (20%) | Neutralizer | Adjust to pH 4.5 |
| Water | Diluent | 92.82 |

Specific Example of Cream Formulation

| Component | Function | Ingredient Range (wt-%) |
|---|---|---|
| (IRM)$_x$(Polymer)$_y$ | Active | 5.0 |
| Isostearic Acid | Oil | 25.0 |
| POLOXAMER 188 | Emulsifier | 1.0 |
| Sorbitan Trioleate | Emulsifier | 1.0 |
| Methylparaben | Preservative | 0.20 |
| Propylparaben | Preservative | 0.10 |
| NaOH (20%) | Neutralizer | Adjust to pH 6 |
| Water | Diluent | Qs to 100 |

Example 23

An IRM was covalently immobilized in a hydrogel using the following procedure.
Preparation of Component A The pH of a solution (2 mL) of 30% (w/v) human serum albumin (HSA) in 0.1 M pH 9.4 carbonate/bicarbonate buffer was adjusted to approximately 4 by the dropwise addition of hydrochloric acid (1 mL of 1 normal (N) HCl). A solution of N-{2-[4-amino-7-(6-aminohexyloxy)-2-ethoxymethyl-1H-imidazo[4,5-c]quinolin-1-yl]-1,1-dimethylethyl}methanesulfonamide in phosphate buffered saline (3.0 mL of 0.6 mg/mL) and a freshly-made solution of EDC in phosphate buffered saline (0.2 mL of 3 mg/mL) were added and the mixture was incubated overnight.

Under 2 hertz (Hz) agitation the mixture was dialyzed through a 3,500 molecular weight cut-off membrane (Spectrum Laboratory Inc., Rancho Domingguez, Calif.) at 4° C. against 0.1 M carbonate/bicarbonate buffer (pH 9.4) for 120 hours, with fresh buffer every day. The concentration of the IRM in the dialyzed buffer was monitored by UV absorption. No detectable IRM (less than 0.1 µg/mL) was found in the final buffer. The resulting mixture was concentrated to 15 wt-% HSA by ultra-filtration through a 50,000 molecular weight cut-off cellulose ester disc membrane (Spectrum Laboratory Inc.).
Preparation of Component B Polyethylene glycol disuccinimidyl succinate (PEG-SS2, prepared according to the method of Example 1 in U.S. Pat. No. 5,583,114) was dissolved in sterile water at 300 mg/mL.
Preparation of Hydrogel Component A (1 mL) and Component B (0.5 mL) were combined. A transparent hydrogel formed in about 10 seconds.

Example 24

Preparation of IRM Grafted Collagen

Collagen fibers (available from Caliochem) were combined with a solution of N-[4-(4-amino-2-propyl-1H-imidazo[4,5-c]quinolin-1-yl)butyl]-N'-[3-(triethoxysilyl)propyl]urea in tetrahydrofuran (0.5-1 wt-%). The mixture was placed in an ultrasonic bath at 45° C. for 24 hours. The collagen fibers were removed from the solution and thoroughly washed with tetrahydrofuran. A sample was analyzed by Time of Flight Secondary Ion Mass Spectroscopy (TOF SIMS). The spectra showed the existence of silicon and of ion fragments of (1-aminobutyl)-2-propyl-1H-imidazo[4,5-c]quinolin-4-amine. Analysis of an untreated collagen fiber did not show either silicon or ion fragments of (1-aminobutyl)-2-propyl-1H-imidazo[4,5-c]quinolin-4-amine.

Example 25

Preparation of IRM Grafted Collagen

Collagen fibers (available from Caliochem) were combined with a solution of 1-aminobutyl)-2-propyl-1H-imidazo[4,5-c]quinolin-4-amine in tetrahydrofuran (5 g of 1 wt-%). 1,3-Dicyclohexylcarbodiimide (50 mg) was added and the mixture was placed in a in an ultrasonic bath at 45° C. for 24 hours. The collagen fibers were removed from the solution and thoroughly washed with tetrahydrofuran. A sample was analyzed by TOF SIMS. The spectra showed the existence of ion fragments of (1-aminobutyl)-2-propyl-1H-imidazo[4,5-c]quinolin-4-amine. Analysis of an untreated collagen fiber did not show ion fragments of (1-aminobutyl)-2-propyl-1H-imidazo[4,5-c]quinolin-4-amine.

Example 26

Preparation of IRM Grafted Poly(ethylene terephthlate) Film

Pieces of poly(ethylene terephthlate) film (available from 3M Company, St. Paul, Minn.) were combined with a solution of 1-(4-aminobutyl)-2-propyl-1H-imidazo[4,5-c]quinolin-4-amine in tetrahydrofuran (2 g of 2.5 wt-%). The mixture was placed in a in an ultrasonic bath at 45° C. for 24 hours. The pieces of film were removed from the solution and thoroughly washed with tetrahydrofuran. Electron Spectroscopy of Chemical Analysis (ESCA), 52° with respect to the sample surface, of a sample showed the existence of nitrogen at 6-7% of the total composition. Analysis of an untreated PET film did not show nitrogen.

Example 27

Preparation of IRM Grafted Acrylate Beads

Oxirane functionalized acrylic beads (160 mg, average 150 µm in diameter, from Sigma Chemical, Cat. No. 0-76280) were suspended in PBS (2 mL) and incubated for 30 minutes. A solution of 1-(4-aminobutyl)-2-butyl-1H-imidazo[4,5-c]quinolin-4-amine in PBS (3 mL of 0.4 g/L) was added. The pH of the mixture was brought up to 9 by the addition of 1N sodium hydroxide. The reaction mixture was shaken (3 Hz) at room temperature for 72 hours. The reaction mixture was then centrifuged at 3000 G for 5 min. The concentration of the IRM in the supernatant was determined by UV-Vis absorption at 247 nanometers (nm). The raw coupling ratio was determined to be 96.5%. After discarding the supernatant, the beads were washed with 6 mL of PBS and centrifuged at 3000 G for 2 min. This procedure was repeated three times. The beads were further washed 3 times with methanol, followed by 2 additional washes with 6 mL of Dulbecco's PBS (DPBS). No detectable IRM (less than 0.1 μg/mL) was found in the final PBS wash. The amount of immobilized IRM was calculated by subtracting the amount found in the washes from the amount that was added to the reaction mixture.

Example 28

Preparation of IRM Grafted Acrylate Beads

The procedure of Example 27 was repeated except that 3 mL of a 0.8 g/mL solution of IRM was used in lieu of 3 mL of a 0.4 g/mL solution of IRM.

Example 29

Preparation of IRM Grafted Acrylate Beads

The procedure of Example 27 was repeated. The beads were further treated with propylamine (7.7 mg) and then washed five times with DPBS.

Example 30

Preparation of IRM Grafted Polystyrene Beads

Carboxylate functionalized polystyrene beads (2 mL of POLYBEAD Carboxylate solution, 2.6% beads, average 10 μm in diameter, from Polysciences Inc, Warrington, Pa.) were washed and then resuspended in 2 mL of PBS buffer (pH 7.4). A solution of 1-(4-aminobutyl)-2-butyl-1H-imidazo[4,5-c]quinolin-4-amine in PBS (3 mL of 0.4 g/L) was added and the pH of the mixture was adjusted to pH 4.5 by addition of 1N hydrochloric acid. A freshly prepared solution of EDC in deionized water (200 μL of 0.3 mg/mL) was added and the mixture was incubated overnight on a shaker operating at 3 Hz. The mixture was then centrifuged at 3000 G for 15 min. The concentration of the IRM in the supernatant was determined by UV-Vis absorption at 247 nm. After discarding the supernatant, the beads were washed with 6 mL of PBS and centrifuged at 3000 G for 2 min. This procedure was repeated three times. The beads were further washed 3 times with methanol, followed by 2 additional washes with 6 mL of Dulbecco's PBS (DPBS). No detectable IRM (less than 0.1 μg/mL) was found in the final PBS wash. The amount of immobilized IRM was calculated by subtracting the amount found in the washes from the amount that was added to the reaction mixture.

Example 31

Preparation of IRM Grafted Polystyrene Beads

The procedure of Example 30 was repeated except that 3 mL of a 0.8 g/mL solution of IRM was used in lieu of 3 mL of a 0.4 g/mL solution of IRM.

Example 32

Preparation of IRM Grafted Polystyrene Beads

The procedure of Example 30 was repeated using N-{2-[4-amino-7-(6-aminohexyloxy)-2-ethoxymethyl-1H-imidazo[4,5-c]quinolin-1-yl]-1,1-dimethylethyl}methanesulfonamide in lieu of 1-(4-aminobutyl)-2-butyl-1H-imidazo[4,5-c]quinolin-4-amine.

Test Data

The beads prepared in Examples 27-31 were tested for their ability to induce cytokines in the following manner. Twenty microliters (20 μL) of a slurry of the beads (80 mg beads/mL PBS) was added to 250 μL of human peripheral blood mononuclear cells ($5 \times 10^5$ cells) in RPMI complete media and incubated overnight. 1:1 dilution duplicates were assayed for IFNα and TNFα concentrations by ELISA. The results are shown in the table below where IFN and TNF are reported in picograms/mL and sd is the standard deviation. Acrylate C1 beads are beads that were incubated with PBS alone. Acrylate C2 beads are beads in which the oxirane functionality was partially quenched by incubation with PBS containing 0.396 mg of propylamine. Acrylate C3 beads are beads in which the oxirane functionality was fully quenched by incubation with PBS containing 7.7 mg of propylamine. Polystyrene control beads are beads that were incubated with PBS alone.

|  | IFNα (1) | IFNα (2) | Ave IFNα | sd | TNFα (1) | TNFα (2) | Ave TNFα | sd |
|---|---|---|---|---|---|---|---|---|
| Acrylate Beads High Dose IRM (Ex 28) | 1006 | 1057 | 1031.1 | 25.6 | 1481.8 | 848.9 | 1165.3 | 316.4 |
| Acrylate Beads Low Dose IRM (Ex 27) | 1086 | 1111 | 1098.2 | 12.3 | 708.3 | 544.6 | 626.5 | 81.9 |
| Acrylate C1 Beads PBS Control | 0 | 0 | 0.0 | 0.0 | 8.8 | 8.1 | 8.5 | 0.3 |
| Acrylate C2 Beads Partially Quenched | 0 | 8 | 4.2 | 4.2 | 346.8 | 278.9 | 312.8 | 34.0 |
| Acrylate C3 Beads Fully Quenched | 0 | 11 | 5.4 | 5.4 | 102.5 | 53.3 | 77.9 | 24.6 |
| Acrylate Beads Low Dose IRM/Quenched (Ex 29) | 1259 | 1233 | 1245.9 | 12.9 | 512.1 | 436.9 | 474.5 | 37.6 |
| Polystyrene Beads High Dose IRM (Ex 31) | 0 | 9 | 4.7 | 4.7 | 55.8 | 61.1 | 58.4 | 2.7 |

-continued

|  | IFNα (1) | IFNα (2) | Ave IFNα | sd | TNFα (1) | TNFα (2) | Ave TNFα | sd |
|---|---|---|---|---|---|---|---|---|
| Polystyrene Beads Low Dose IRM (Ex 30) | 9 | 0 | 4.7 | 4.7 | 55.5 | 45.9 | 50.7 | 4.8 |
| Polystyrene Control Beads | 41 | 0 | 20.7 | 20.7 | 38.1 | 31.1 | 34.6 | 3.5 |

The beads prepared in Example 19 were tested for their ability to induce cytokines using the method described above for the beads of Examples 27-31. The results are shown in the table below where IFN and TNF are reported in picograms/mL and sd is the standard deviation. Control DYNABEADS are beads that were treated with buffer alone.

|  | IFNα (1) | IFNα (2) | Ave IFNα | Sd | TNFα (1) | TNFα (2) | Ave TNFα | sd |
|---|---|---|---|---|---|---|---|---|
| IRM on DYNABEADS (Ex. 19) | 1148.7 | 888.6 | 1018.7 | 130.0 | 33.2 | 45.8 | 39.5 | 6.3 |
| Control DYNABEADS | 5.7 | 1.4 | 3.5 | 2.1 | 26.1 | 17.2 | 21.7 | 4.5 |

The particles of Examples 2-11, 15, and 16 were tested in a single experiment using the method described above for the beads of Examples 27-31 and did not induce significant amounts of either interferon alpha or tumor necrosis factor alpha at the concentrations tested.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. An IRM-support complex comprising an IRM compound that is a TLR agonist selected from the group consisting of TLR6, TLR7, TLR8, and combinations thereof, and selected from the group consisting of imidazoquinoline amines; tetrahydroimidazoquinoline amines; and imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; 1H-imidazo dimers fused to pyridine amines, quinoline amines, tetrahydroquinoline amines, naphthyridine amines, or tetrahydronaphthyridine amines; and combinations thereof; covalently bonded to a macromolecular support material wherein the macromolecular support material has an average largest dimension of at least 1 nm.

* * * * *